United States Patent
Wakamori et al.

(10) Patent No.: US 11,921,081 B2
(45) Date of Patent: Mar. 5, 2024

(54) ODOR SENSOR AND METHOD FOR MANUFACTURING ODOR SENSOR

(71) Applicants: HAMAMATSU PHOTONICS K.K., Hamamatsu (JP); National University Corporation TOYOHASHI UNIVERSITY OF TECHNOLOGY, Toyohashi (JP)

(72) Inventors: Toshiki Wakamori, Hamamatsu (JP); Shinichi Nakahigashi, Hamamatsu (JP); Kazuaki Sawada, Toyohashi (JP)

(73) Assignees: HAMAMATSU PHOTONICS K.K., Hamamatsu (JP); National University Corporation TOYOHASHI UNIVERSITY OF TECHNOLOGY, Toyohashi (JP)

( * ) Notice: Subject to any disclaimer, the term of this patent is extended or adjusted under 35 U.S.C. 154(b) by 581 days.

(21) Appl. No.: 17/255,014

(22) PCT Filed: May 27, 2019

(86) PCT No.: PCT/JP2019/020959
§ 371 (c)(1),
(2) Date: Dec. 22, 2020

(87) PCT Pub. No.: WO2020/012800
PCT Pub. Date: Jan. 16, 2020

(65) Prior Publication Data
US 2021/0262975 A1 Aug. 26, 2021

(30) Foreign Application Priority Data
Jul. 12, 2018 (JP) .................. 2018-132452

(51) Int. Cl.
*G01N 27/414* (2006.01)
*G01N 33/00* (2006.01)

(52) U.S. Cl.
CPC ..... *G01N 27/4141* (2013.01); *G01N 33/0031* (2013.01)

(58) Field of Classification Search
USPC ....................................... 73/31.05
See application file for complete search history.

(56) References Cited

U.S. PATENT DOCUMENTS

2014/0200842 A1    7/2014  Dasai et al.
2017/0173262 A1*   6/2017  Veltz ............... G16H 20/17
(Continued)

FOREIGN PATENT DOCUMENTS

JP    H8-152423 A     6/1996
JP    2006-242900 A   9/2006
(Continued)

OTHER PUBLICATIONS

Shinmyo, Naoya et al., "Gas Distribution Imaging by Charge-Transfer-Type Sensor Arrays with Polyaniline Sensitive Layer," Lecture preprints of the 64th JSAP spring meeting, 16p-416-6, 2017, p. 11-330 (including English language translation).
(Continued)

*Primary Examiner* — Clayton E. LaBalle
*Assistant Examiner* — Warren K Fenwick
(74) *Attorney, Agent, or Firm* — Faegre Drinker Biddle & Reath LLP

(57) ABSTRACT

A smell sensor includes an ion sensor in which a sensing section provided with a sensitive film configured to change a potential in accordance with a state of a measurement target is formed on a semiconductor substrate; a substance adsorption film disposed on the sensitive film and configured to change the state with adsorption of a smell substance; and a reference electrode configured to apply a reference voltage to the substance adsorption film. The reference electrode is disposed to be separated from the sensitive film and not to
(Continued)

overlap the sensing section when viewed in a thickness direction of the semiconductor substrate.

20 Claims, 12 Drawing Sheets

(56) References Cited

U.S. PATENT DOCUMENTS

| | | | | |
|---|---|---|---|---|
| 2022/0196593 A1* | 6/2022 | Mizuno | ............... | G01N 27/4141 |
| 2022/0260519 A1* | 8/2022 | Mizuno | ............... | G01N 33/0031 |

FOREIGN PATENT DOCUMENTS

| | | |
|---|---|---|
| JP | 2007-292734 A | 11/2007 |
| JP | 2010-127757 A | 6/2010 |
| JP | 2012-058065 A | 3/2012 |
| JP | 2012-078180 A | 4/2012 |
| JP | 2012-207991 A | 10/2012 |
| JP | 2012-233876 A | 11/2012 |
| JP | 6083753 A | 2/2017 |
| TW | 201124719 A | 7/2011 |
| WO | WO 2013/024791 A1 | 2/2013 |
| WO | WO-2017/018449 A1 | 2/2017 |
| WO | WO-2017/122338 A1 | 7/2017 |

OTHER PUBLICATIONS

Shinmyo, Naoya et al., "Development of Potentiometric Miniature Gas Sensor Arrays Feasible for Small Olfactory Chips and Gas Recognition From Their Response Patterns," Chemical Sensors, 2017, vol. 33, supplement B, p. 55-p. 57.

Masato Futagawa, "Fabricatieh of a 128×128 Pixels Charge Transfer Type Hydrogen Ion Image Sensor", IEEE Transactions on Electron Devices, vol. 60, No. 8, 2013, p. 2634-2639.

International Preliminary Report on Patentability dated Jan. 21, 2021 for PCT/JP2019/020959.

* cited by examiner

ODOR SENSOR AND METHOD FOR MANUFACTURING ODOR SENSOR

TECHNICAL FIELD

The present disclosure relates to a smell sensor and a method for manufacturing a smell sensor.

BACKGROUND ART

The sensor disclosed in Non-Patent Document 1 is known as a smell sensor having sensitivity to a smell. In the above sensor, a polyaniline sensitive film (a smell substance adsorption film) is formed on an ion sensitive film ($Si_3N_4$) of a so-called charge transfer type pH image sensor. In the above sensor, a mesh electrode is provided on a surface of the polyaniline sensitive film to achieve both application of a predetermined reference voltage (Vgate) to the polyaniline sensitive film and gas exposure to the polyaniline sensitive film (that is, adsorption of a smell substance).

CITATION LIST

Non-Patent Document

[Non-Patent Document 1] Naoya Shinmyo, Tatsuya Iwata, Kenichi Hashizume, Shunichiro Kuroki, Kazuaki Sawada (2017), Gas distribution imaging by charge transfer type sensor arrays using polyaniline sensitive film, 64th JSAP Spring Meeting, 16p-416-6.

SUMMARY OF INVENTION

Technical Problem

In the sensor described in Non-Patent Document 1, the mesh electrode is also provided on a sensing section. Therefore, there is a problem that a smell cannot be properly detected in the sensing section (pixels) directly below the mesh electrode.

An object of an aspect of the present disclosure is to provide a smell sensor capable of appropriately detecting a smell and a manufacturing method thereof.

Solution to Problem

A smell sensor according to an aspect of the present disclosure includes an ion sensor in which at least one sensing section provided with a sensitive film configured to change a potential in accordance with a state of a measurement target is formed on a substrate; a substance adsorption film as the measurement target, disposed on the sensitive film and configured to change the state with adsorption of a smell substance; and a reference electrode configured to apply a reference voltage to the substance adsorption film. The reference electrode is disposed to be separated from the sensitive film and not to overlap the sensing section when viewed in a thickness direction of the substrate.

According to the smell sensor described above, the smell can be detected based on the potential change of the sensitive film according to the change of the state of the substance adsorption film when the substance adsorption film adsorbs the smell substance. To carry out such smell detection (measurement), it is necessary to apply the reference voltage to the substance adsorption film. As a configuration for this, for example, a configuration in which an electrode (for example, a mesh electrode) is disposed on the upper surface of the substance adsorption film (including a portion that overlaps the sensing section when viewed in the thickness direction of the substrate) is conceivable. However, in this configuration, since the smell substance is less likely to be adsorbed on the portion of the substance adsorption film immediately below the electrode (the portion that is hidden by the electrode and is not exposed to the outside), there is a problem that the smell cannot be appropriately detected by the sensing section immediately below the electrode. On the other hand, in the smell sensor, the reference electrode for applying the reference voltage to the substance adsorption film is disposed to be separated from the sensitive film and not to overlap the sensing section when viewed in the thickness direction of the substrate. This solves the problem in a case in which the mesh electrode as described above is disposed. Therefore, according to the smell sensor, it is possible to appropriately detect the smell.

The smell sensor may further include a passivation layer provided to cover the ion sensor, wherein the substance adsorption film may be provided to cover the passivation layer, wherein the sensitive film may be in contact with the substance adsorption film through a first opening provided in the passivation layer, and wherein the reference electrode may be provided between the substance adsorption film and the substrate, and may be in contact with the substance adsorption film through a second opening provided in the passivation layer. As described above, in a case in which a configuration in which the reference electrode is embedded inside the substance adsorption film is employed, it is possible to easily create the reference electrode by arranging the metal wiring using, for example, the CMOS process or the like. This makes it possible to create the reference electrode with high reproducibility. Further, since the reference electrode can be created in the CMOS process, it is possible to prevent the generation of an extra workload for forming the reference electrode. Further, the voltage supply to the reference electrode can be facilitated via a pad embedded in the ion sensor.

The smell sensor may further include a passivation layer provided to cover the ion sensor, wherein the substance adsorption film may be provided to cover the passivation layer, wherein the sensitive film may be in contact with the substance adsorption film through an opening provided in the passivation layer, and wherein the reference electrode may be disposed at an outer edge portion of the sensing section when viewed in the thickness direction of the substrate, and may include a portion exposed inside the opening and in contact with the substance adsorption film. In this case, the reference voltage can be appropriately applied to the substance adsorption film inside the opening provided on the sensing section.

The reference electrode may be provided on at least a surface of the substance adsorption film opposite to the substrate. For example, in a case in which the electrode provided on an outer surface of the substance adsorption film (a surface opposite to the substrate) together with an embedded electrode is provided as the reference electrode as described above, it is possible to apply the reference voltage to the substance adsorption film more reliably and stably by increasing a contact area between the substance adsorption film and the reference electrode. On the other hand, the reference electrode may be provided only on the outer surface of the substance adsorption film, and in this case, the processes such as the creation of the embedded electrode and the formation of the opening (the second opening) of the passivation layer can be omitted. Further, an arrangement pitch of the sensing sections on the substrate can be reduced by omitting the embedded electrodes. As a result, the smell sensor can be downsized. Alternatively, in a case in which smell distribution measurement (imaging) is performed, spatial resolution can be improved.

The ion sensor may have a plurality of sensing sections arranged one-dimensionally or two-dimensionally on the substrate, and one substance adsorption film may be disposed on the sensitive films of two or more sensing sections. In this case, the plurality of sensing sections can be associated with one substance adsorption film. Accordingly, for example, by using a statistical value (for example, an average value) of the output values of the plurality of sensing sections, it is possible to reduce variation in the sensitivity in the measurement. Further, even if some of the sensing sections are defective, the measurement can be performed using other sensing sections.

The ion sensor may have a plurality of sensing sections arranged one-dimensionally or two-dimensionally on the substrate, and a plurality of substance adsorption films may be disposed on the sensitive films of different sensing sections. In this case, for example, by providing a plurality of substance adsorption films that react with different smell substances on one ion sensor, it is possible to detect a complex smell pattern based on the output values of the sensing section corresponding to each substance adsorption film. Note that it is also conceivable to use a plurality of ion sensors provided with different substance adsorption films, but in this case, it may be necessary to perform measurement in consideration of individual differences (variations in sensitivity) between the ion sensors. Further, the increase in the number of necessary ion sensors increases the overall size of the device. On the other hand, according to the configuration in which the plurality of substance adsorption films are disposed on one ion sensor as described above, such a problem can be solved. Further, even in a case in which a plurality of substance adsorption films of the same kind are provided on one ion sensor, when one of the substance adsorption films in the ion sensor does not function properly, an effect that the measurement can be continued based on the output value of the sensing section corresponding to another substance adsorption film is exhibited.

The ion sensor may have a plurality of sensing sections arranged one-dimensionally or two-dimensionally on the substrate, and the reference electrode may be disposed such that distances between the sensitive film of each of the plurality of sensing sections and the reference electrode are substantially the same. The inventor of the present invention has confirmed that the sensitivity of the sensing section can be influenced by the distance between the sensitive film of the sensing section and the reference electrode. Therefore, the reference electrodes are disposed such that the distances between the sensitive film of each sensing section and the reference electrode are substantially the same as described above, and thus the sensitivity of each sensing section can be made uniform.

A method for manufacturing a smell sensor according to another aspect of the present disclosure includes a step of preparing an ion sensor in which a sensing section provided with a sensitive film configured to change a potential in accordance with a state of a measurement target is formed on a substrate; a step of disposing, on the sensitive film, a substance adsorption film as the measurement target configured to change the state with adsorption of a smell substance; and a step of disposing the reference electrode configured to apply a reference voltage to the substance adsorption film to be separated from the sensitive film and not to overlap the sensing section when viewed in a thickness direction of the substrate.

According to the above-described manufacturing method, it is possible to appropriately manufacture the smell sensor exhibiting the above-described effects.

In the manufacturing method, the substance adsorption film may be provided to cover the sensitive film and the reference electrode after the reference electrode is disposed. Accordingly, a smell sensor having a structure in which the reference electrode is embedded inside the substance adsorption film can be obtained.

The manufacturing method may further include a step of forming a passivation layer on the ion sensor to cover the reference electrode after the reference electrode is disposed; and a step of forming, in the passivation layer, a first opening for exposing at least a part of the sensitive film to the outside and a second opening for exposing at least a part of the reference electrode to the outside. Further, the substance adsorption film may be provided to cover the passivation layer after the first opening and the second opening are formed, may be in contact with the sensitive film through the first opening, and may be in contact with the reference electrode through the second opening. In this case, even in a case in which the reference electrode and the sensing section are disposed at relatively distant positions when viewed in the thickness direction, it is possible to realize a configuration in which the reference voltage can be applied to the substance adsorption film disposed on the sensitive film.

The manufacturing method may further include a step of forming a passivation layer on the ion sensor to cover the reference electrode after the reference electrode is disposed at an outer edge portion of the sensing section when viewed in the thickness direction of the substrate; and a step of forming, in the passivation layer, an opening for exposing at least a part of the sensitive film and at least a part of the reference electrode to the outside. Further, the substance adsorption film may be provided to cover the passivation layer after the opening is formed, and may be in contact with the sensitive film and the reference electrode in the second opening. In this case, by disposing the reference electrode at the outer edge portion of the sensing section viewed in the thickness direction, and thus by forming the common opening in the reference electrode and the sensitive film, it is possible to realize a configuration in which the reference voltage can be applied to the substance adsorption film disposed on the sensitive film.

At least a part of the reference electrode may be provided to cover a part of the substance adsorption film after the substance adsorption film is disposed. Accordingly, a smell sensor having a structure in which at least a part of the reference electrode is disposed outside the substance adsorption film can be obtained.

Advantageous Effects of Invention

According to the aspect of the present disclosure, it is possible to provide a smell sensor capable of appropriately detecting a smell and a manufacturing method thereof.

DESCRIPTION OF EMBODIMENTS

Hereinafter, embodiments of the present disclosure will be described in detail with reference to the accompanying drawings. In the description of the drawings, the same or equivalent elements will be denoted by the same reference signs, without redundant description. The present disclosure is not limited to these examples, but is defined by the scope of the claims, and is intended to include meanings equivalent to the scope of the claims and all modifications within the scope.

First Embodiment

Figure 1:
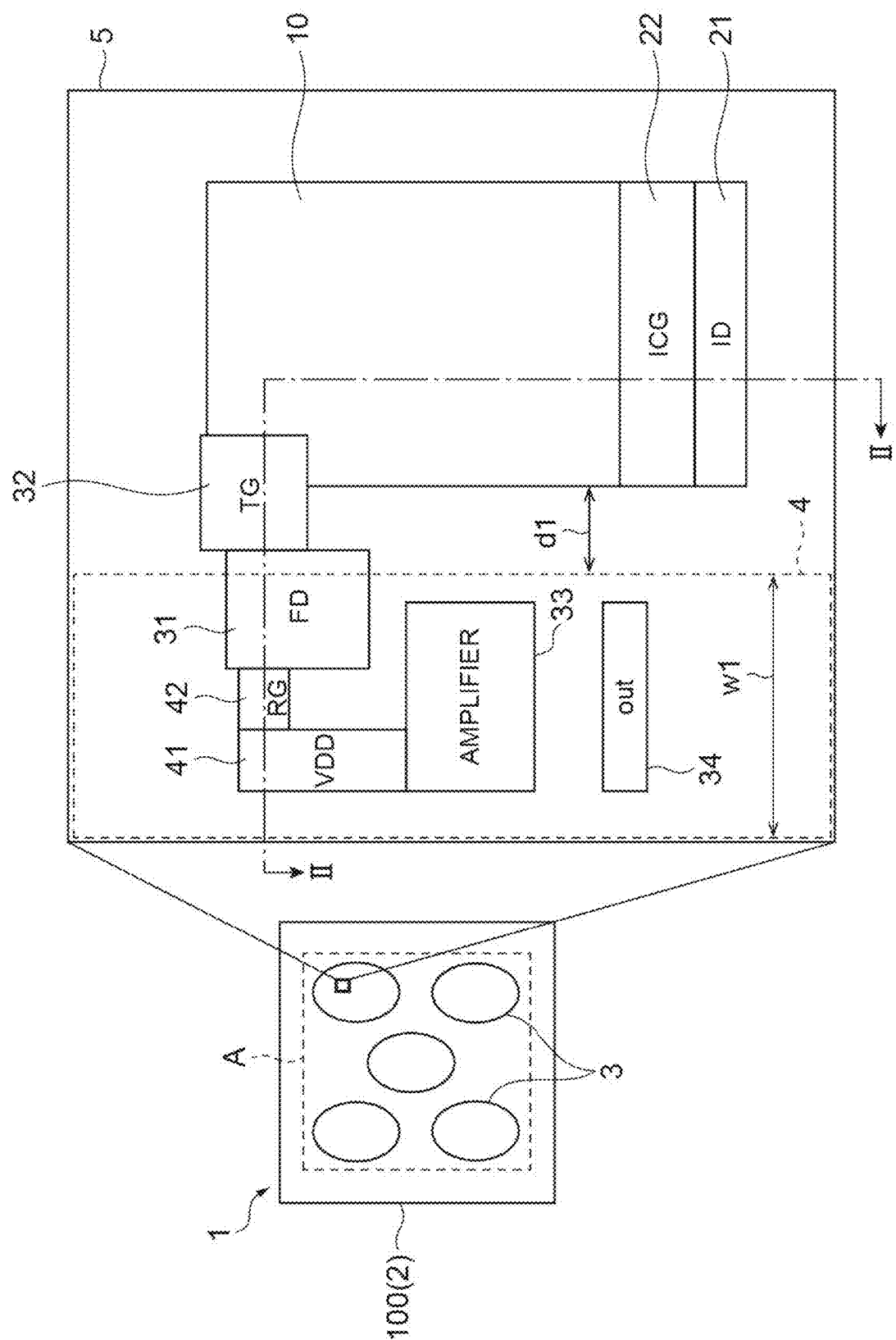
FIG. 1 is a schematic plan view of a smell sensor according to a first embodiment.

FIG. 1 is a schematic plan view of a smell sensor 1 according to a first embodiment. As shown in FIG. 1, the smell sensor 1 includes an ion sensor 2, a plurality of (five in this case) substance adsorption films 3 provided on the ion sensor 2, and a reference electrode 4 for applying a reference voltage Vref to the substance adsorption film 3.

The ion sensor 2 is a sensor in which a plurality of detection units 5 arranged two-dimensionally are formed on a semiconductor substrate 100. The ion sensor 2 is a so-called charge transfer type CMOS image sensor. The plurality of detection units 5 are two-dimensionally arranged in a pixel formation region A provided on a chip of the ion sensor 2 (a rectangular region provided in a central portion of a chip in the present embodiment) in M rows and N columns (for example, 256 rows and 256 columns), to form a pixel array. M and N are integers of 2 or more. One detection unit 5 corresponds to one detection unit (pixel). The size of one detection unit 5 (the pixel size) is, for example, 30 μm×30 μm.

Each substance adsorption film 3 is disposed (formed) to straddle the plurality of detection units 5 in the pixel formation region A. The substance adsorption film 3 is a thin film of which a state (for example, electrical characteristics such as impedance) is changed with adsorption of a predetermined smell substance. Here, an "smell" is something that stimulates the olfactory sense of a living thing such as a human or animal, and an "smell substance" is a chemical substance that causes the smell (for example, collection of a specific molecule alone or a group of molecules at a predetermined concentration). As the substance adsorption film 3, for example, a polyaniline sensitive film or the like can be used. The detection unit 5 provided with the substance adsorption film 3 among the detection units 5 disposed in the pixel formation region A functions as a unit detection element capable of detecting the smell. Note that the substance adsorption film 3 may be provided on the entire pixel formation region A (that is, all the detection units 5 disposed in the pixel formation region A), or there may be detection units 5 on which the substance adsorption film 3 is not provided.

Figure 2:
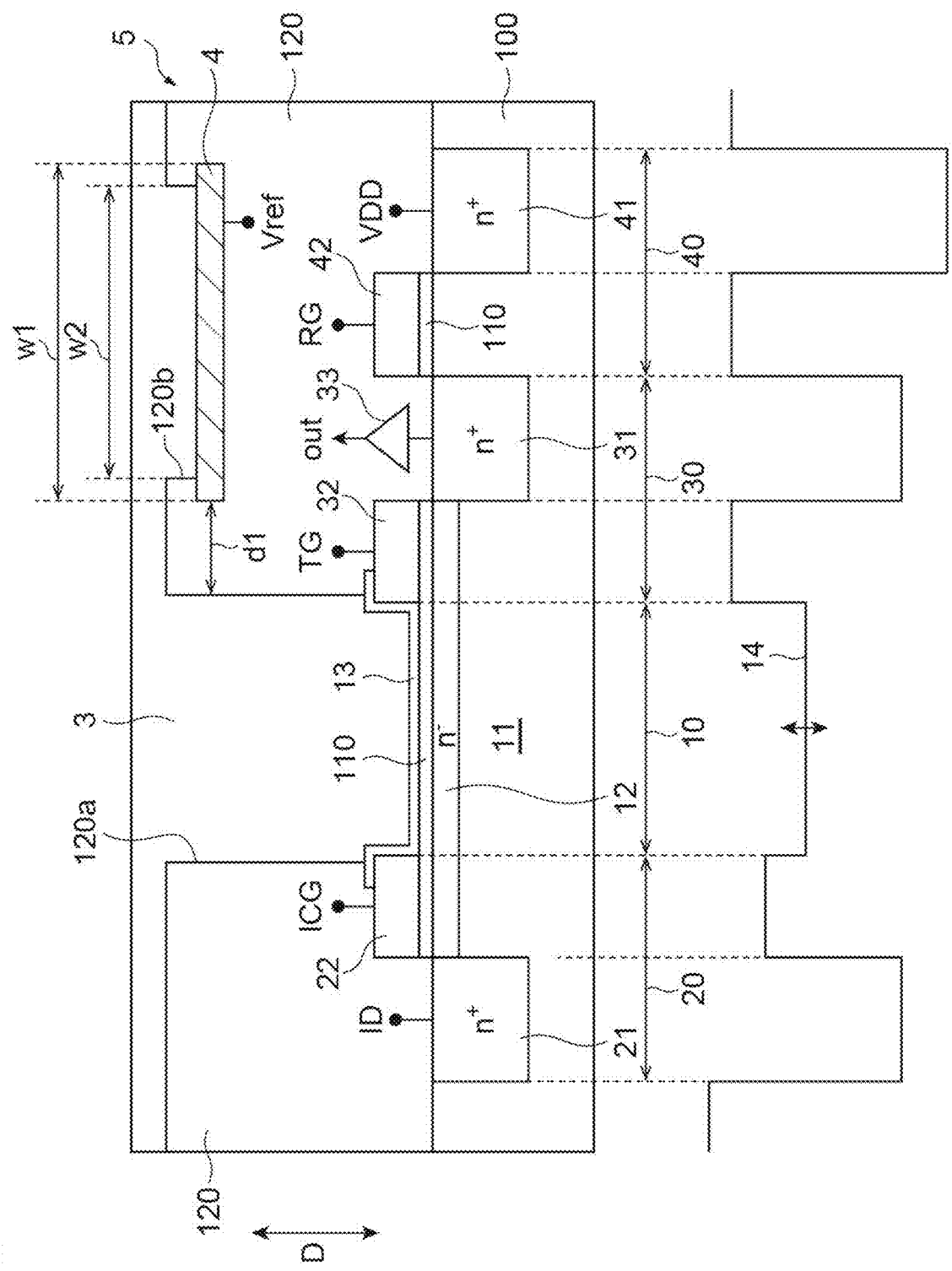
FIG. 2 is a view schematically showing a cross-sectional configuration of a detection unit.

The right part of FIG. 1 schematically shows a layout example common to each detection unit 5. FIG. 2 is a view schematically showing a cross-sectional configuration of the detection unit 5 along line II-II in FIG. 1. As shown in the drawings, each detection unit 5 is formed on one main surface side of the semiconductor substrate 100 (a substrate). The semiconductor substrate 100 is a first conductive type (an n-type as an example) semiconductor substrate formed of, for example, silicon. In each detection unit 5, along the main surface of the semiconductor substrate 100, an injection diode portion 21 (hereinafter referred to as an "ID portion 21"), a floating diffusion portion 31 (hereinafter referred to as an "FD portion 31"), and a reset drain portion 41 (hereinafter referred to as an "RD portion 41"), which are each a first conductive type region, are formed. A second conductive type (a p-type as an example) diffusion layer 11 is formed between the ID portion 21 and the FD portion 31 of the semiconductor substrate 100. A first conductive type region 12 doped in a first conductive type is formed on a surface of the diffusion layer 11.

An input control gate electrode 22 (hereinafter referred to as an "ICG electrode 22"), a transfer gate electrode 32 (hereinafter referred to as a "TG electrode 32"), and a reset gate electrode 42 (hereinafter referred to as an "RG electrode 42") are formed on the main surface of the semiconductor substrate 100 via an insulating protective film 110. As the protective film 110, for example, $SiO_2$ or the like can be used. Further, an amplifier (a signal amplifier) 33 that amplifies an out signal according to the amount of charges accumulated in the FD portion 31, and an output circuit 34 that outputs the out signal amplified by the amplifier 33 to a measuring unit (not shown) are provided on the main surface of the semiconductor substrate 100.

A sensitive film 13 is provided in a region between the ICG electrode 22 and the TG electrode 32 via the protective film 110. The sensitive film 13 is an ion sensitive film having a property of a potential (a membrane potential) changing according to the state of a measurement target disposed on the sensitive film 13. In the present embodiment, the substance adsorption film 3 is the measurement target. As the sensitive film 13, for example, $Si_3N_4$ or the like can be used. The sensitive film 13 covers a part of the ICG electrode 22 and the TG electrode 32 so that the ICG electrode 22 and the TG electrode 32 do not come into contact with the substance adsorption film 3. Thus, the sensitive film 13 is integrally formed over the ICG electrode 22 to the TG electrode 32. However, the sensitive film 13 may be provided only between the ICG electrode 22 and the TG electrode 32, or may be formed not to cover a part of the ICG electrode 22 and the TG electrode 32. That is, the sensitive film 13 may be formed only on the protective film 110 between the ICG electrode 22 and the TG electrode 32.

An insulating passivation layer 120 is formed on the main surface of the semiconductor substrate 100 to cover members provided on the main surface of the semiconductor substrate 100. As the passivation layer 120, for example, $Si_3N_4$ or the like can be used. The substance adsorption film 3 is provided to cover the passivation layer 120. The passivation layer 120 has an opening 120a (a first opening) for exposing an upper surface of the sensitive film 13 to the outside. The sensitive film 13 is in contact with the substance adsorption film 3 through the opening 120a.

The reference electrode 4 is provided inside the substance adsorption film 3 (that is, between the substance adsorption film 3 and the semiconductor substrate 100). As shown in FIGS. 1 and 2, the reference electrode 4 is disposed to be separated from the sensitive film 13 and not to overlap the sensitive film 13 when viewed in a thickness direction D of the semiconductor substrate 100. The reference electrode 4 is metal wiring formed by a CMOS process, for example. As shown in FIG. 1, in each detection unit 5, the reference electrode 4 is disposed at a position separated from a sensing section 10 on one side (a left side in FIG. 1) of the sensing section 10 (a region where the sensitive film 13 is provided between the ICG electrode 22 and the TG electrode 32, which will be described in detail later) when viewed from the thickness direction D. That is, the reference electrode 4 is disposed not to come into physical contact with the sensing section 10 (mainly the sensitive film 13). The reference electrode 4 extends in a vertical direction in FIG. 1 to be parallel to one side surface of the sensing section 10. A distance d1 between the sensing section 10 and the reference electrode 4 when viewed in the thickness direction D is, for example, 3 µm. A width w1 of the reference electrode 4 (that is, a width of the metal wiring forming the reference electrode 4) is, for example, 10.5 µm. The reference electrode 4 is arranged, for example, in a second wiring layer that is farther from the main surface of the semiconductor substrate 100 than a first wiring layer. In the first wiring layer, for example, metal wiring (not shown) for supplying a voltage to the ICG electrode 22, the TG electrode 32, the RG electrode 42, and the like is provided. That is, the reference electrode 4 is arranged in the second wiring layer closer to an outer surface of the passivation layer 120 than the first wiring layer.

The reference electrode 4 may be formed of a material capable of coming into contact with the substance adsorption film 3 and applying a voltage thereto. As the reference electrode 4, for example, Al—Si—Cu or the like can be used. The reference voltage Vref is supplied to the reference electrode 4 from an electrode pad (not shown) included in the ion sensor 2. The passivation layer 120 has an opening 120b (a second opening) for exposing an upper surface of the reference electrode 4 to the outside. The reference electrode 4 is in contact with the substance adsorption film 3 through the opening 120a. Accordingly, the reference voltage Vref is applied to the substance adsorption film 3 at a contact portion between the reference electrode 4 and the substance adsorption film 3. In the example of FIG. 2, the upper surface of the reference electrode 4 is located at a position recessed toward the semiconductor substrate 100 side with respect to an upper surface of the passivation layer 120. Further, an opening width w2 of the opening 120b (a width of a portion of the reference electrode 4 which is exposed to the outside) is smaller than a width w1 of the reference electrode 4. The opening width w2 is, for example, 8 µm. However, the reference electrode 4 may be provided so that the upper surface of the reference electrode 4 is continuous (flatly connected) with a portion of the passivation layer 120 at which the opening 120b is not formed. In this case, the width w1 of the reference electrode 4 and the opening width w2 match.

A depth of the opening 120a is larger than a depth of the opening 120b. That is, the sensitive film 13 is disposed at a position recessed toward the semiconductor substrate 100 side with respect to the reference electrode 4.

Next, the functional configuration and operation principle of the detection unit 5 will be described. The detection unit 5 includes a sensing section 10, a supply section 20, a movement and accumulation section 30, and a removal section 40. Note that, in this embodiment, the charges are electrons.

The sensing section 10 is a region where the sensitive film 13 is exposed to the outside (that is, to the substance adsorption film 3) through the opening 120a of the passivation layer 120. More specifically, the sensing section 10 is a region between the ICG electrode 22 and the TG electrode 32, where the sensitive film 13 faces the first conductive type region 12 with the protective film 110 interposed therebetween. That is, the sensing section 10 is a sensing region configured by the diffusion layer 11, the first conductive type region 12, the protective film 110, and the sensitive film 13 described above which are stacked. When the substance adsorption film 3 adsorbs a predetermined smell substance, a change in the state (for example, impedance) of the substance adsorption film 3 occurs. Then, in the sensitive film 13, a change in a potential according to the change in the state occurs. A depth of a potential well 14 of the diffusion layer 11 facing the sensitive film 13 changes according to the change of the potential of the sensitive film 13.

The supply section 20 includes the ID portion 21 and the ICG electrode 22 described above. The ID portion 21 is a portion for injecting the charges into the potential well 14. The ICG electrode 22 is a portion that controls the amount of charges to be injected from the ID portion 21 into the potential well 14. For example, by lowering a potential of the ID portion 21 and adjusting a voltage of the ICG electrode 22, it is possible to supply the charges with which the ID portion 21 is charged to the potential well 14.

The movement and accumulation section 30 includes the TG electrode 32 and the FD portion 31. The TG electrode 32 is a portion for transferring the charges from the potential well 14 to the FD portion 31. The FD portion 31 is a portion that accumulates the charges transferred from the potential well 14. Specifically, by changing a voltage of the TG electrode 32, a potential of a region of the semiconductor substrate 100 which faces the TG electrode 32 (hereinafter referred to as a "TG region") is changed, and the charges filled in the potential well 14 can be transferred to and accumulated in the FD portion 31.

The removal section 40 includes the RG electrode 42 and the RD portion 41. The removal section 40 is a portion for resetting (removing) the charges accumulated in the FD portion 31. Specifically, by changing a voltage of the RG electrode 42, a potential of a region of the semiconductor substrate 100 which faces the RG electrode 42 (hereinafter referred to as an "RG region") is changed, and the charges accumulated in the FD portion 31 can be discharged to the RD portion 41 (VDD).

Figure 3:
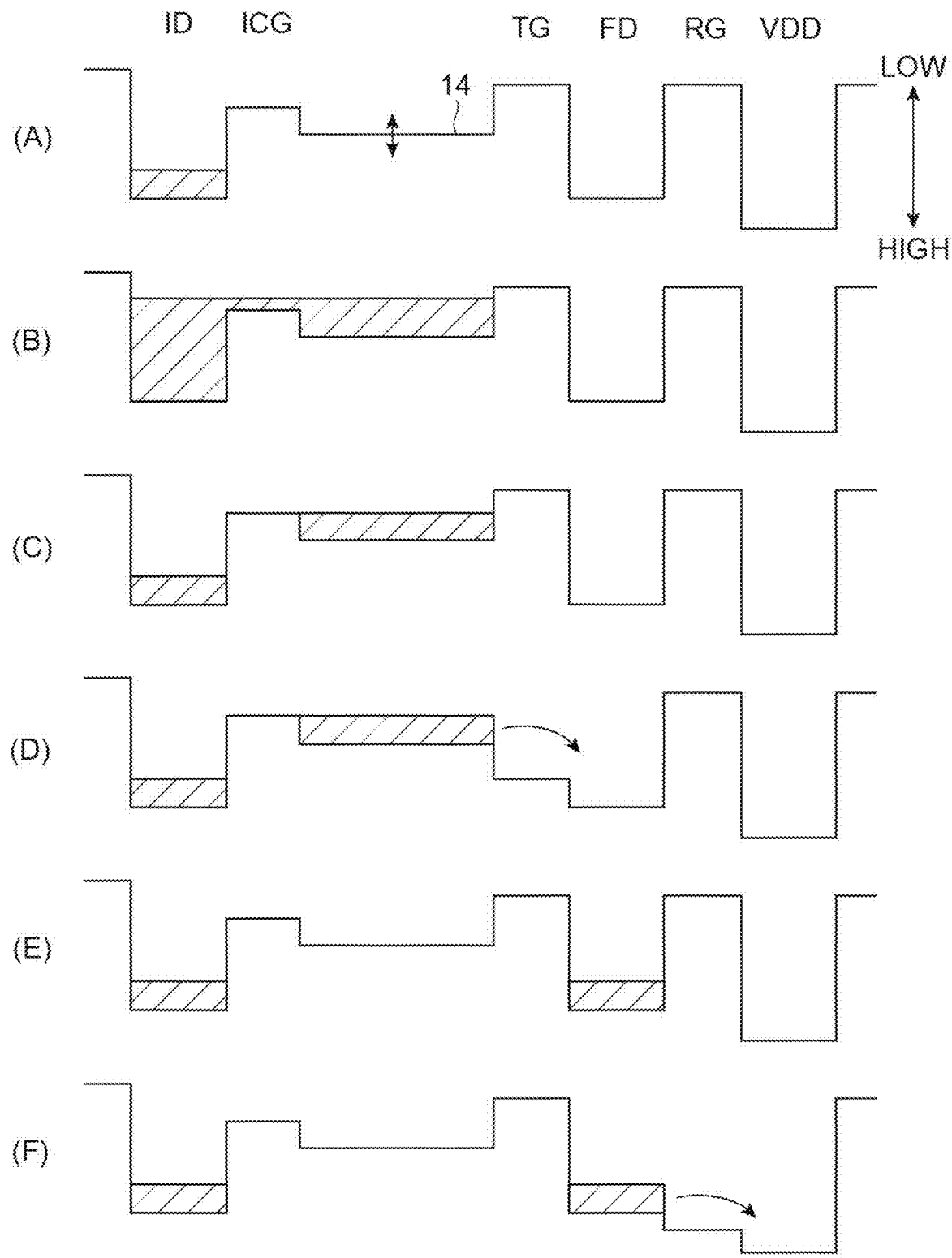
FIG. 3 is a diagram showing an example of an operation of the detection unit.

FIG. 3 is a diagram showing an example of a basic operation of the detection unit 5. As shown in (A) of FIG. 3, when the state (for example, impedance) of the portion of the substance adsorption film 3 which is measurement target on which the smell substance is adsorbed changes, a change in the potential of the sensitive film 13 located immediately below the portion occurs, and the depth of the potential well 14 changes according to the change in the potential. Subsequently, as shown in (B) of FIG. 3, the potential of the ID portion 21 is lowered, and thus the ID portion 21 is charged with the charges. The charges with which the ID portion 21 is charged are injected into the potential well 14 beyond a region of the semiconductor substrate 100 which faces the ICG electrode 22 (hereinafter referred to as an "ICG region"). At this time, a potential of the TG region is controlled to be lower than the potential of the ID portion 21. Therefore, the charges which are injected into the potential well 14 do not reach the FD portion 31 beyond the TG region.

Subsequently, as shown in (C) of FIG. 3, the potential of the ID portion 21 is restored (raised), and thus the charges are extracted from the ID portion 21. As a result, the charges scooped by the ICG region remain in the potential well 14. The amount of charges left in the potential well 14 corresponds to the depth of the potential well 14 (that is, the impedance change of the substance adsorption film 3).

Subsequently, as shown in (D) of FIG. 3, the voltage of the TG electrode 32 is raised, and thus the charges left in the potential well 14 are transferred to the FD portion 31. After that, the voltage of the TG electrode 32 is restored, and thus a state shown in (E) of FIG. 3 is realized. In such a state, a signal (an out signal) according to the amount of charges accumulated in the FD portion 31 is output to a measuring unit (not shown) via the amplifier 33 and the output circuit 34. Accordingly, the smell detected in the substance adsorption film 3 (that is, the smell substance adsorbed on the substance adsorption film 3) is measured as a change in an output voltage in the measuring unit. Subsequently, as shown in (F) of FIG. 3, the voltage of the RG electrode 42 is raised, and thus the charges accumulated in the FD portion 31 are discharged to the RD portion 41. The RD portion 41 is connected to a VDD power supply. Accordingly, the negatively charged charges are sucked into the RD portion 41.

Note that the above-described operations of (B) to (E) of FIG. 3 may be repeated a plurality of times. Accordingly, the amount of charges accumulated in the FD portion 31 can be increased and the out signal can be amplified according to the number of repetitions. Further, the amplifier 33 may be omitted when the out signal is amplified with such a repeated operation.

Figure 4:
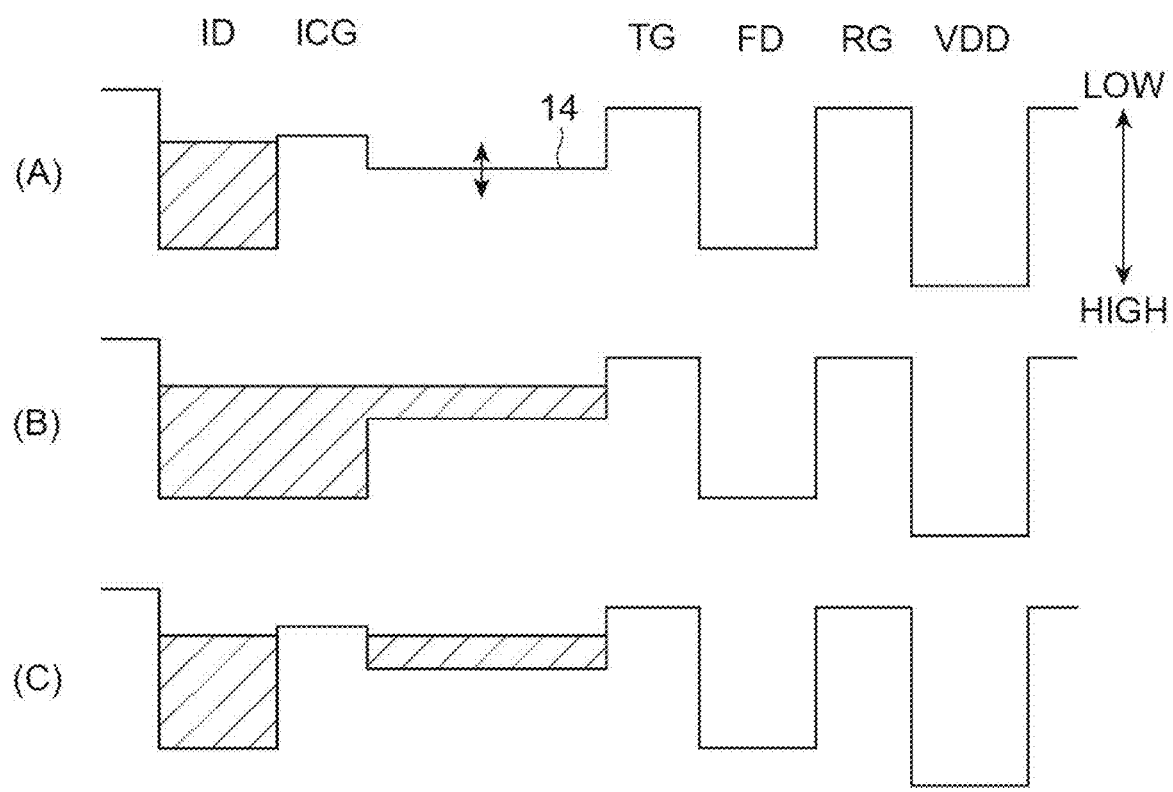
FIG. 4 is a diagram showing another example of an operation of the detection unit.

However, a method of injecting charges into the potential well 14 is not limited to the example of FIG. 3 described above. For example, as shown in FIG. 4, the potential of the ID portion 21 is kept constant and the voltage of the ICG electrode 22 is adjusted, and thus the charges having the same potential as the ID portion 21 may be injected into the potential well 14. Specifically, as shown in (A) of FIG. 4, the potential of the ID portion 21 is set to a constant value lower than the potential of the potential well 14 and higher than the potential of the TG region. On the other hand, a potential of the ICG region is made lower than the potential of the ID portion 21. Subsequently, as shown in (B) of FIG. 4, the potential of the ICG region is made higher than the potential of the potential well 14, and thus the charges are supplied from the ID portion 21 to the potential well 14. Subsequently, as shown in (C) of FIG. 4, the potential of the ICG region is made lower than the potential of the ID portion 21 again, and thus the charges scooped by the ICG region remain in the potential well 14. As described above, the charges having the same potential as that of the ID portion 21 are accumulated in the potential well 14. Note that the subsequent operations in the example of FIG. 4 are similar to the operations of (D) to (F) of FIG. 3.

Next, an example of a method for manufacturing the smell sensor 1 will be described. First, the ion sensor 2 in which the sensing section 10 provided with the sensitive film 13 is formed on the semiconductor substrate 100 is prepared. Subsequently, the reference electrode 4 is disposed to be separated from the sensitive film 13 and not to overlap the sensing section 10 when viewed in the thickness direction D. Subsequently, the passivation layer 120 is formed on the ion sensor 2 (that is, on the main surface of the semiconductor substrate 100). Note that the passivation layer 120 may be formed stepwise by being divided a plurality of times. For example, after a first passivation layer that covers the semiconductor substrate 100 and the sensitive film 13 is formed, the reference electrode 4 may be arranged on the first passivation layer, and then a second passivation layer that covers the reference electrode 4 may be formed, to form the passivation layer 120. In this way, the passivation layer 120 is formed on the ion sensor 2 to cover the reference electrode 4. Subsequently, in the passivation layer 120, the opening 120a for exposing at least a part of the sensitive film 13 (in the present embodiment, a part of the upper surface of the sensitive film 13) to the outside, and the opening 120b for exposing at least a part of the reference electrode 4 (in the present embodiment, a part of the upper surface of the reference electrode 4) to the outside are formed by etching or the like. Subsequently, the substance adsorption film 3 is disposed on the sensitive film 13. More specifically, the substance adsorption film 3 is provided to cover the passivation layer 120, is in contact with the sensitive film 13 through the opening 120a, and is in contact with the reference electrode 4 through the opening 120b. Thus, in the above manufacturing method, the substance adsorption film 3 is provided to cover the sensitive film 13 and the reference electrode 4 after the reference electrode 4 is disposed. As described above, the smell sensor 1 including the plurality of detection units 5 having the structure shown in FIG. 2 (that is, the structure in which the reference electrode 4 is embedded inside the substance adsorption film 3) can be obtained. Further, in the above manufacturing method, even in a case in which the reference electrode 4 and the sensing section 10 are disposed at relatively distant positions when viewed in the thickness direction D, the opening 120a and the opening 120b corresponding to the reference electrode 4 and the sensitive film 13, respectively, are formed, and thus it is possible to realize a configuration in which the reference voltage Vref can be applied to the substance adsorption film 3 disposed on the sensitive film 13.

Next, the function and effect of the smell sensor 1 will be described. According to the smell sensor 1 described above, the smell can be detected based on the potential change of the sensitive film 13 according to the change of the state of the substance adsorption film 3 (for example, the change of impedance) when the substance adsorption film 3 adsorbs the smell substance. To carry out such smell detection (measurement), it is necessary to apply the reference voltage Vref to the substance adsorption film 3. As a configuration for this, for example, as in the configuration described in Non-Patent Document 1, a configuration (see (A) of FIG. 5) in which an electrode (for example, a mesh electrode) is disposed on the upper surface of the substance adsorption film 3 (including a portion that overlaps the sensing section 10 when viewed in the thickness direction D) is conceivable. However, in this configuration, since the smell substance is less likely to be adsorbed on the portion of the substance adsorption film 3 immediately below the electrode (the portion that is hidden by the electrode and is not exposed to the outside), there is a problem that the smell cannot be appropriately detected by the sensing section 10 immediately below the electrode. On the other hand, in the smell sensor 1, the reference electrode 4 for applying the reference voltage Vref to the substance adsorption film 3 is disposed to be separated from the sensitive film 13 and not to overlap the sensing section 10 when viewed in the thickness direction D. This solves the problem in a case in which the mesh electrode as described above is used.

Further, for example, in a case in which the sensitivity to the smell is caused by the change in the impedance of the substance adsorption film 3, if the sensitive film 13 and the reference electrode 4 are brought too close to each other, the sensitivity to the smell is likely to be lost. On the other hand, in the smell sensor 1, the reference electrode 4 is disposed to be separated from the sensitive film 13 and not to overlap the sensing section 10 when viewed in the thickness direction D, and thus it is possible to prevent the sensitive film 13 and the reference electrode 4 from coming too close to each other. As a result, it is possible to prevent the sensitive film 13 from being unable to properly detect the smell due to the sensitive film 13 and the reference electrode 4 being too close to each other. Therefore, according to the smell sensor 1, it is possible to appropriately detect the smell.

Here, if the reference electrode 4 is disposed to face the ICG electrode 22 or the TG electrode 32, the potential (Vref) of the reference electrode 4 may be disturbed due to the ICG electrode 22 or the TG electrode 32 (particularly, the TG electrode 32 of which the voltage is changed in a pulse shape before and after the transfer of the charges to the FD portion 31). On the other hand, as shown in FIGS. 1 and 2, in the smell sensor 1, the reference electrode 4 is disposed not to overlap either of the ICG electrode 22 and the TG electrode 32 when viewed in the thickness direction D. Accordingly, it is possible to prevent the above-mentioned problems from occurring.

Further, in the smell sensor 1, the substance adsorption film 3 is provided to cover the passivation layer 120. The sensitive film 13 is in contact with the substance adsorption film 3 through the opening 120a provided in the passivation layer 120. The reference electrode 4 is provided between the substance adsorption film 3 and the semiconductor substrate 100, and is in contact with the substance adsorption film 3 that has entered the opening 120b through the opening 120b provided in the passivation layer 120. As described above, in a case in which a configuration in which the reference electrode 4 is embedded inside the substance adsorption film 3 is employed, it is possible to easily create the reference electrode 4 by arranging the metal wiring using, for example, the CMOS process or the like. This makes it possible to create the reference electrode 4 with high reproducibility. Further, since the reference electrode 4 can be created in the CMOS process, it is possible to prevent the generation of an extra workload for forming the reference electrode 4. Further, the voltage supply to the reference electrode 4 can be facilitated via the electrode pad (not shown) embedded in the ion sensor 2.

Further, in the smell sensor 1, the ion sensor 2 has a plurality of sensing sections 10 (detection units 5) arranged two-dimensionally on the semiconductor substrate 100. One substance adsorption film 3 is disposed on two or more sensing sections 10. That is, one substance adsorption film 3 is disposed to straddle a plurality of unit detection elements (pixels). In this case, the plurality of sensing sections 10 can be associated with one substance adsorption film 3. Accordingly, for example, by using a statistical value (for example, an average value) of the output values (the out signals) of the plurality of sensing sections 10, it is possible to reduce variation in the sensitivity in the measurement. Further, even in a case in which some of the sensing sections 10 corresponding to one substance adsorption film 3 are defective (that is, in a case in which defective pixels are generated), by using other sensing sections 10 (that is, other detection units 5), it is possible to carry out measurement (smell detection) using the substance adsorption film 3. Further, it is also possible to perform imaging measurement (measurement of two-dimensional smell distribution) based on the output values of the plurality of sensing sections 10. Accordingly, for example, it is possible to find a diffusion direction and it is also possible to discover the source of the smell in the sample by disposing the sample near the smell sensor 1.

Further, in the smell sensor 1, a plurality of substance adsorption films 3 are disposed on different sensing sections 10 (detection units 5). That is, a plurality of (five in the present embodiment) substance adsorption films 3 are formed independently of each other on one ion sensor 2 (that is, one sensor chip). For example, by providing a plurality of substance adsorption films 3 that react with different smell substances (that is, a plurality of substance adsorption films having different characteristics) on one ion sensor 2, it is possible to detect a complex smell pattern based on the output values (the out signals) of the sensing section 10 corresponding to each substance adsorption film 3. Note that it is also conceivable to use a plurality of ion sensors provided with different substance adsorption films 3, but in this case, it may be necessary to perform measurement in consideration of individual differences (variations in sensitivity) between the ion sensors. Further, the increase in the number of necessary ion sensors increases the overall size of the device. On the other hand, according to the configuration in which the plurality of substance adsorption films 3 are disposed on one ion sensor 2 as described above, such a problem can be solved. Further, even in a case in which a plurality of substance adsorption films 3 of the same kind are provided on one ion sensor 2, when one of the substance adsorption films 3 in the ion sensor 2 does not function properly, an effect that the measurement can be continued based on the output value of the sensing section 10 corresponding to another substance adsorption film 3 is exhibited.

Here, the plurality of substance adsorption films 3 provided on one ion sensor 2 may be a plurality of substance adsorption films having different component amounts (contents) of the same material (in the present embodiment, polyaniline) or a plurality of substance adsorption films formed of different materials. By using the plurality of substance adsorption films 3 having different component amounts or materials as described above, it is possible to detect various smell substances based on a combination of the measurement results of the substance adsorption films 3. For example, in a case in which table information (smell database) in which combinations of the measurement results of the plurality of substance adsorption films are associated with specific smell substances is prepared in advance, it is possible to specify the smell substance corresponding to each combination of the measurement results of the plurality of substance adsorption films 3 by referring to the table information.

Further, the inventor of the present invention has confirmed that the sensitivity of the sensing section 10 can be influenced by the distance between the sensitive film 13 of the sensing section 10 and the reference electrode 4. Therefore, in the smell sensor 1, the reference electrode 4 is disposed such that the distances between the sensitive film 13 of each of the plurality of sensing sections 10 and the reference electrode 4 are substantially the same. Specifically, as described above, in each detection unit 5, the reference electrode 4 is disposed such that the distance d1 between the sensing section 10 and the reference electrode 4 when viewed in the thickness direction D is constant (for example, 3 μm). Accordingly, the sensitivity of each sensing section 10 can be made uniform.

Figure 5:
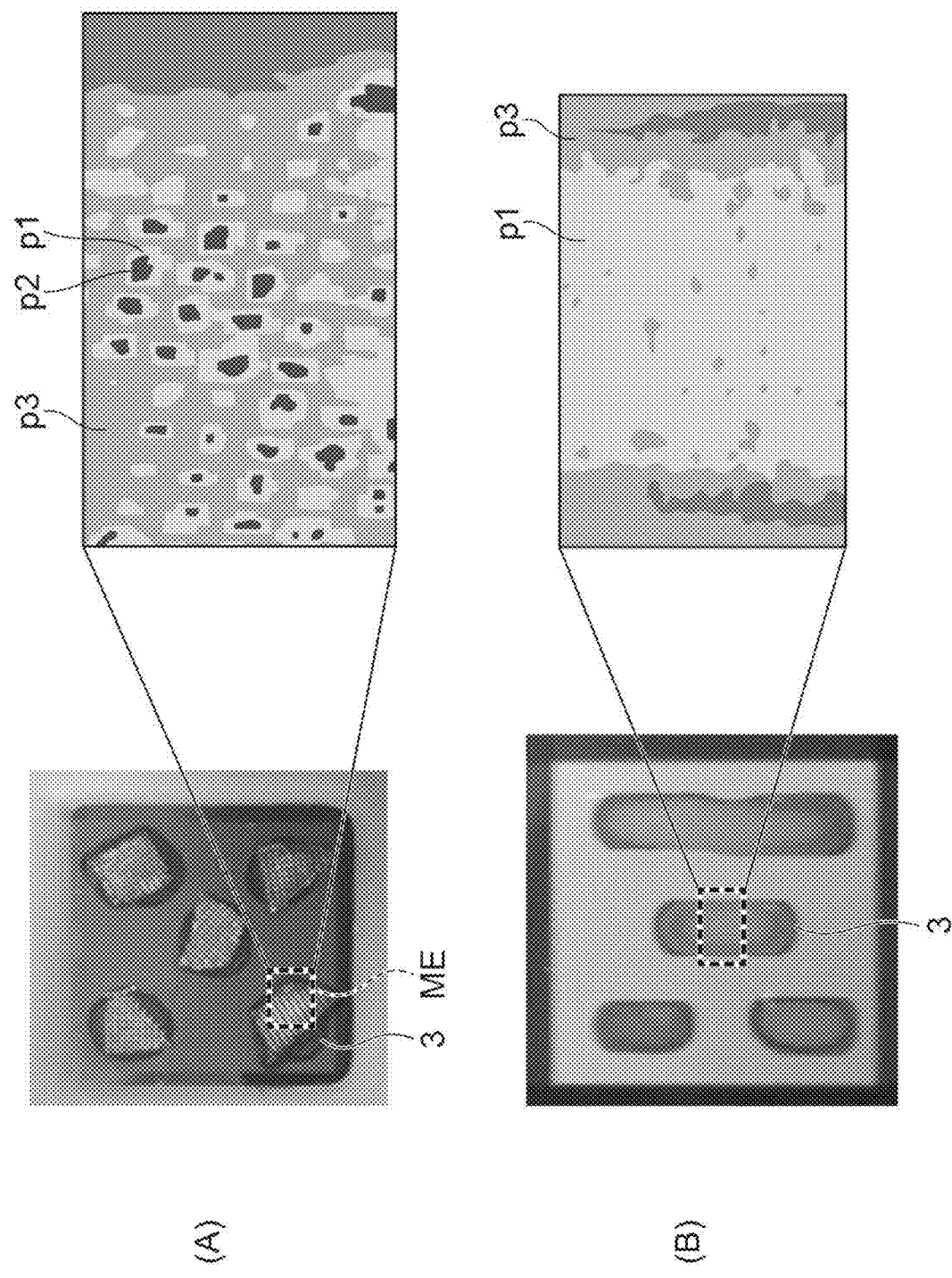
FIG. 5 is a diagram showing measurement results of a smell sensor of a comparative example and measurement results of a smell sensor of an example.

The above effect will be further described with reference to FIG. 5. (A) of FIG. 5 is a diagram in which the measurement result (sensitivity) of each pixel (each sensing section) when a smell sensor according to a comparative example (hereinafter, simply referred to as a "comparative example") is exposed to ammonia gas is represented with gradation. (B) of FIG. 5 is a diagram in which the measurement result (sensitivity) of each pixel (each sensing section) when a smell sensor according to an example (hereinafter, simply referred to as an "example") is exposed to ammonia gas is represented with gradation. The comparative example is a smell sensor in which a mesh electrode ME is disposed on the substance adsorption film 3 as in the structure described in Non-Patent Document 1. The example is a smell sensor that employs an embedded electrode (a reference electrode 4) as in the smell sensor 1 described above. In FIG. 5, a high sensitivity region p1 having the lightest color (a color close to white) and a low sensitivity region p2 having a color close to black are regions corresponding to the sensing section showing the sensitivity of a certain level or higher (that is, regions where the smell of the ammonia gas is detected). The high sensitivity region p1 is a region showing a higher sensitivity than that of the low sensitivity region p2. On the other hand, a non-sensitive region p3, which is represented by a color slightly darker than the high sensitivity region p1, is a region corresponding to the sensing section that does not show sensitivity (a non-sensitive pixel).

As shown in (A) of FIG. 5, in the comparative example, the non-sensitive region p3 is formed in a mesh shape. Such a mesh-shaped non-sensitive region p3 is a region corresponding to a portion covered with the mesh electrode ME. Such a mesh-shaped non-sensitive region p3 is considered to be formed because the smell substance is not adsorbed on the portion of the substance adsorption film 3 which is covered with the mesh electrode ME. On the other hand, the smell sensitivity is obtained in the region corresponding to the portion not covered with the mesh electrode ME. However, the low sensitivity region p2 is formed in a portion distant from the mesh electrode ME (a central portion of a region of which four sides are surrounded by the mesh electrode ME), and the high sensitivity region p1 is formed in a portion relatively close to the mesh electrode ME (an edge portion of a region of which four sides are surrounded by the mesh electrode ME). That is, it is confirmed that there is a difference in sensitivity between the sensing section disposed at a position relatively close to the mesh electrode ME and the sensing section disposed at a position relatively distant from the mesh electrode ME.

On the other hand, as shown in (B) of FIG. 5, in the example configured such that the mesh electrode is not provided, and the distances between the sensitive film 13 of each sensing section 10 and the reference electrode 4 are substantially the same, a substantially uniform high sensitivity region p1 is formed. From such measurement results, the effect of disposing the sensitive films 13 of each of the plurality of sensing sections 10 and the reference electrode 4 so that the distances therebetween are substantially the same is confirmed.

Figure 6:
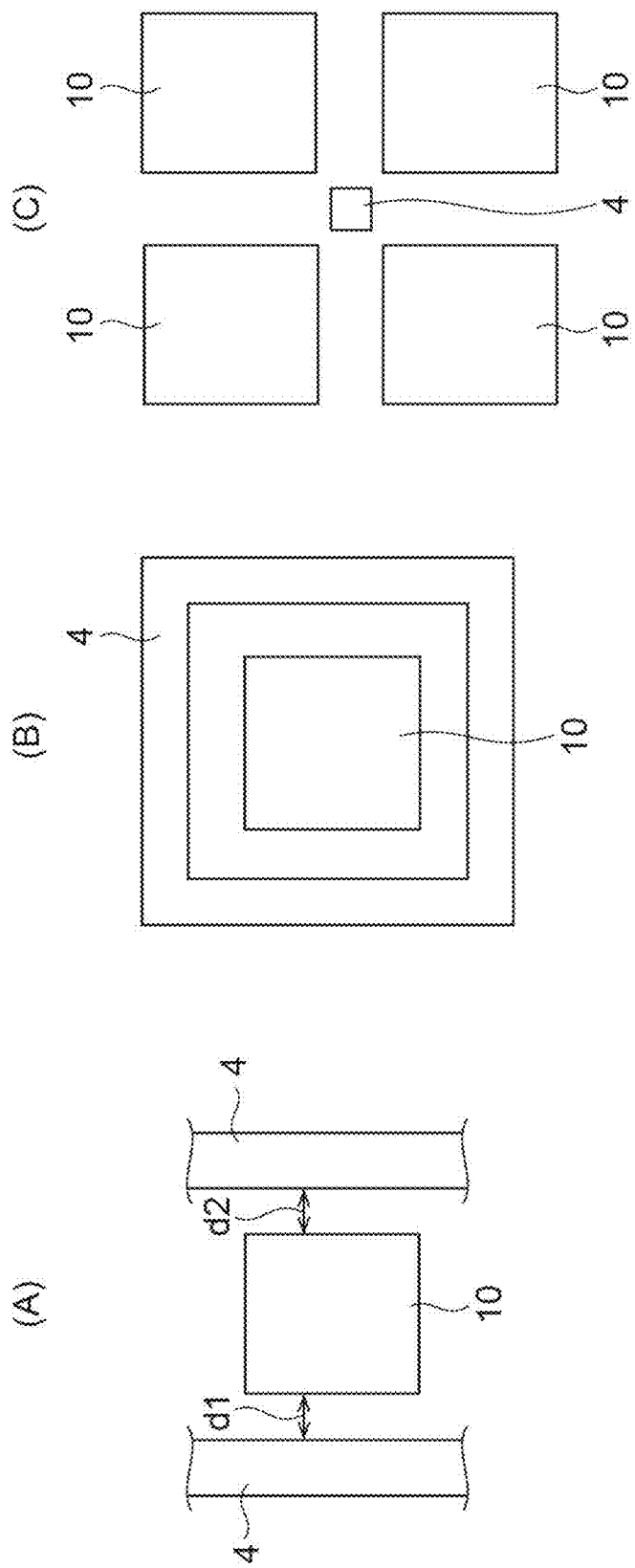
FIG. 6 is a diagram showing an arrangement configuration example of a reference electrode.

More specifically, in the present embodiment and the above-described example, the detection units 5 of the layout shown in the right part of FIG. 1 are arranged two-dimensionally (in a grid shape), and thus, as shown in (A) of FIG. 6, when viewed in the thickness direction D, a pair of reference electrodes 4 extending in parallel to each other are disposed to interpose both sides of one sensing section 10. Further, a distance d2 between the sensing section 10 of one detection unit 5 and the reference electrode 4 disposed to pass over a detection unit 5 on a right side of the one detection unit 5 is adjusted to be substantially the same as the distance d1.

However, the layout of the reference electrode 4 is not limited to the above example. For example, as shown in (B) of FIG. 6, the reference electrode 4 may be disposed to surround four sides of the sensing section 10 of each detection unit 5 when viewed in the thickness direction D. Further, as shown in (C) of FIG. 6, when viewed in the thickness direction D, for four sensing sections 10 (four pixels) disposed in 2 rows and 2 columns, a common reference electrode 4 (for example, an electrode formed in a rectangular shape when viewed in the thickness direction D) may be disposed at a central position of a region defined by the four pixels. In any layout, the positional relationship between the sensitive film 13 of each sensing section 10 (each pixel) and the reference electrode 4 is made common. Accordingly, the distances between the sensitive film 13 of each sensing section 10 and the reference electrode 4 adjacent to the sensitive film 13 can be made substantially the same. As a result, the sensitivity of each sensing section 10 can be made uniform. However, in a case in which it is not necessary to make the sensitivity of each sensing section 10 uniform, or in a case in which it is desired to have a sensitivity difference (sensitivity gradient) between the sensing sections 10, the reference electrode 4 may be disposed such that the positional relationship (distance) between the sensitive film 13 and the reference electrode 4 is different for each sensing section 10 (for each pixel).

First Modification Example of Reference Electrode

Figure 7:
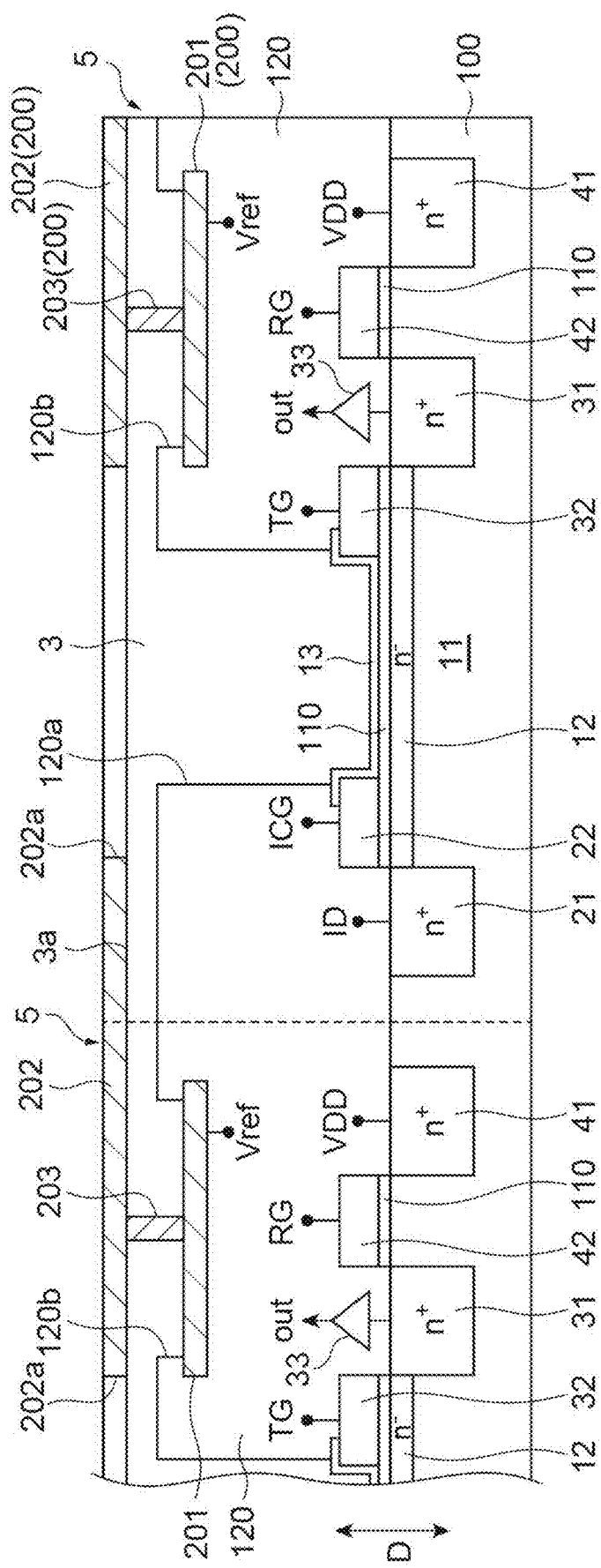
FIG. 7 is a view schematically showing a cross-sectional configuration of a detection unit including a first modification example of a reference electrode.

FIG. 7 is a view schematically showing a cross-sectional configuration of a detection unit 5 including a reference electrode 200 of a first modification example. The reference electrode 200 of the first modification example has a second electrode 202 and a third electrode 203 in addition to a first electrode 201 configured similarly to the reference electrode 4 described above.

The second electrode 202 is provided on an outer surface 3a of the substance adsorption film 3 (that is, a surface opposite to the semiconductor substrate 100). The second electrode 202 is a membrane-structured (membrane-like) electrode member formed along the outer surface 3a of the substance adsorption film 3. The second electrode 202 is created using, for example, a MEMS process. The second electrode 202 is provided with an opening 202a for exposing the portion of the substance adsorption film 3 which corresponds to the sensing section 10 to the outside. In the present embodiment, the opening 202a is provided to include the sensing section 10, the ICG electrode 22, and the TG electrode 32 when viewed in the thickness direction D. That is, the second electrode 202 is disposed not to overlap the sensing section 10, the ICG electrode 22, and the TG electrode 32 when viewed in the thickness direction D. The second electrode 202 can be formed in a grid shape to surround the four sides of each sensing section 10 when viewed in the thickness direction D, for example, as shown in (B) of FIG. 6.

The third electrode 203 is an electrode member that electrically connects the first electrode 201 and the second electrode 202 to each other through the opening 120b of the passivation layer 120 and supports the second electrode 202. As an example, the third electrode 203 is a wall-shaped member that is disposed in a widthwise center of the first electrode 201 and extends along the first electrode 201. Alternatively, the third electrode 203 may be configured with one or more columnar members. A smell sensor including such a reference electrode 200 is obtained by carrying out, for example, the manufacturing method of the smell sensor 1 including the reference electrode 4 described above, and then further carrying out a step of forming the second electrode 202 and the third electrode 203 by a MEMS process or the like. That is, in the method for manufacturing the smell sensor including the reference electrode 200, at least a part of the reference electrode (here, the second electrode 202 and the third electrode 203) is provided to cover a part of the substance adsorption film 3 after the substance adsorption film 3 is disposed. Accordingly, a smell sensor having a structure in which at least a part of the reference electrode is disposed outside the substance adsorption film 3 can be obtained.

According to the reference electrode 200 of the first modification example, it is possible to apply the reference voltage Vref to the substance adsorption film 3 more reliably and stably by increasing the contact area between the substance adsorption film 3 and the reference electrode.

Second Modification Example of Reference Electrode

Figure 8:
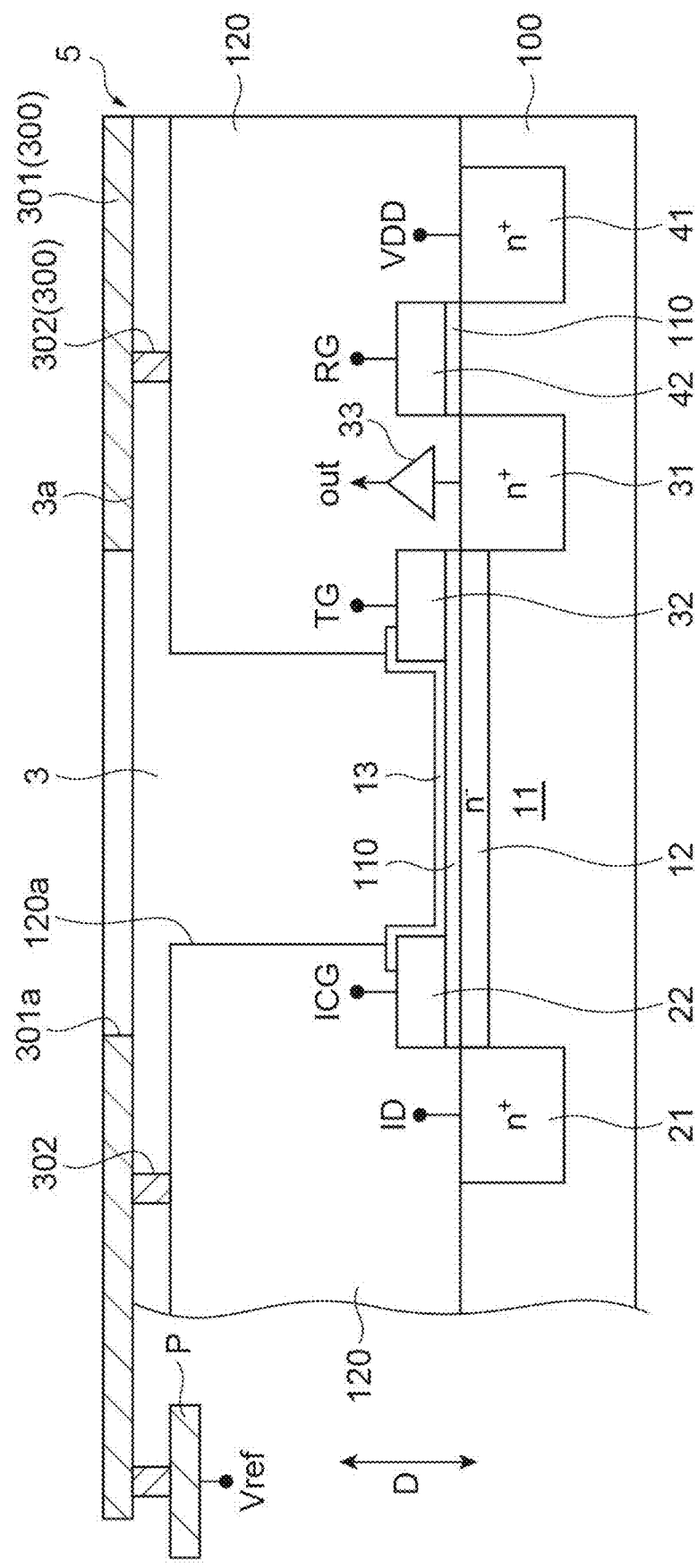
FIG. 8 is a view schematically showing a cross-sectional configuration of a detection unit including a second modification example of a reference electrode.

FIG. 8 is a view schematically showing a cross-sectional configuration of a detection unit 5 including a reference electrode 300 of a second modification example. The reference electrode 300 of the second modification example has a first electrode 301 and a second electrode 302 that are configured similarly to the second electrode 202 and the third electrode 203 of the reference electrode 200. On the other hand, in the reference electrode 300, embedded electrodes such as the reference electrode 4 and the first electrode 201 described above are not created in a stage of the CMOS process. Therefore, a lower end of the second electrode 302 is disposed on the upper surface of the passivation layer 120. In the reference electrode 300, the first electrode 301 is electrically connected to an electrode pad P provided at an arbitrary location outside the pixel array in the ion sensor 2, and thus the reference voltage Vref is applied from the electrode pad P.

A smell sensor including the reference electrode 300 is obtained by carrying out a step of forming the first electrode 301 and the second electrode 302 by a MEMS process or the like while omitting the step of disposing the reference electrode 4 and the step of forming the opening 120b in the method for manufacturing the smell sensor 1 including the reference electrode 4 described above, for example. That is, in the method for manufacturing the smell sensor including the reference electrode 300, at least a part of the reference electrode (here, the first electrode 301 and the second electrode 302) is provided to cover a part of the substance adsorption film 3 after the substance adsorption film 3 is disposed. Accordingly, a smell sensor having a structure in which at least a part of the reference electrode is disposed outside the substance adsorption film 3 can be obtained.

According to the reference electrode 300 of the second modification example, in the CMOS process, it is possible to omit the processes such as the creation of the embedded electrodes such as the reference electrode 4 and the first electrode 201 and the formation of the opening 120b described above. Further, an arrangement pitch of the sensing sections 10 (detection units 5) on the semiconductor substrate 100 can be reduced by omitting the embedded electrodes. As a result, the smell sensor 1 can be downsized. Alternatively, in a case in which smell distribution measurement (imaging) is performed, spatial resolution can be improved.

Third Modification Example of Reference Electrode

Figure 9:
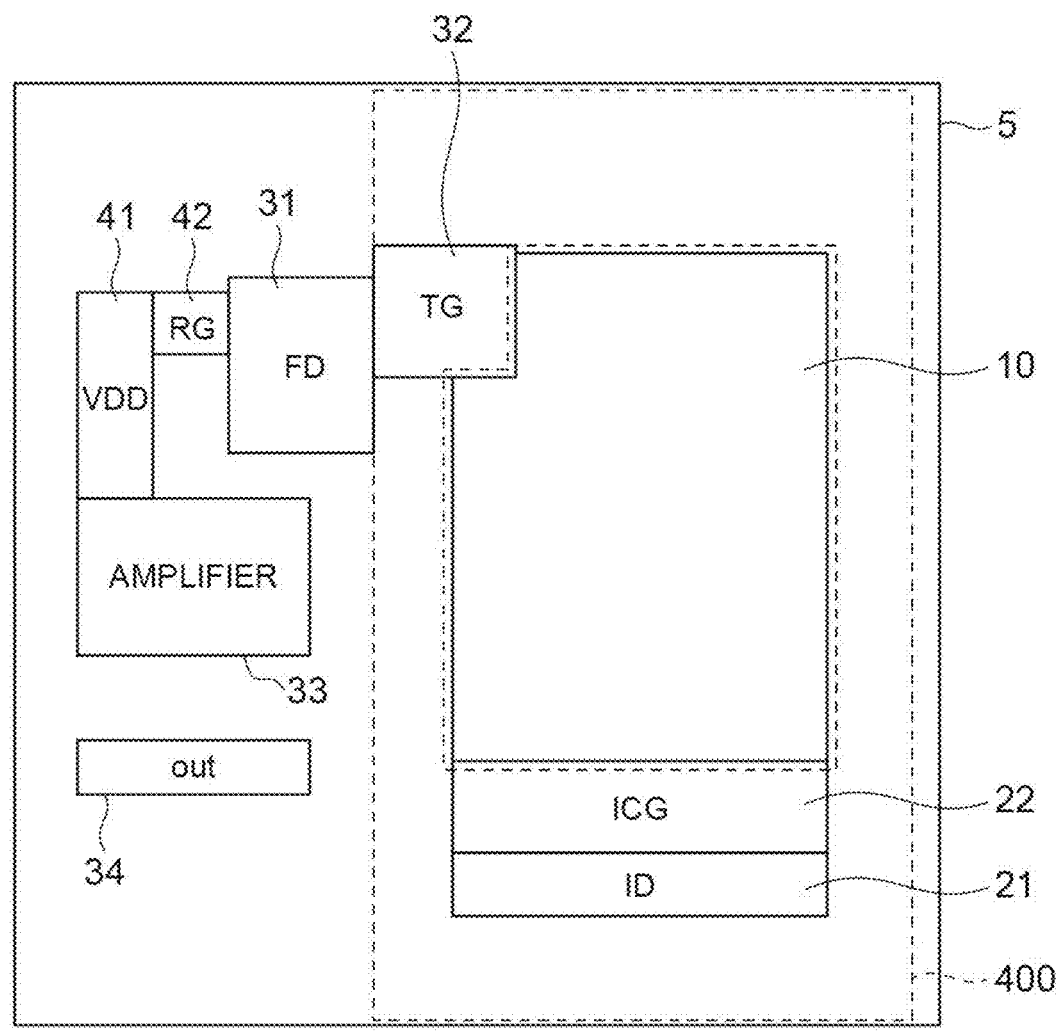
FIG. 9 is a view showing a layout example of a detection unit including a third modification example of a reference electrode.

A third modification example of the reference electrode will be described with reference to FIGS. 9 and 10. FIG. 9 is a view showing a layout example of a detection unit 5 including a reference electrode 400 of the third modification example. As shown in FIG. 9, the reference electrode 400 is disposed at an outer edge portion (an outer peripheral portion) of the sensing section 10 when viewed in the thickness direction D. That is, in each detection unit 5, the reference electrode 4 and the opening 120b described above are not formed, but the reference electrode 400 (metal wiring) formed in an annular shape to surround the sensing section 10 is arranged.

Figure 10:
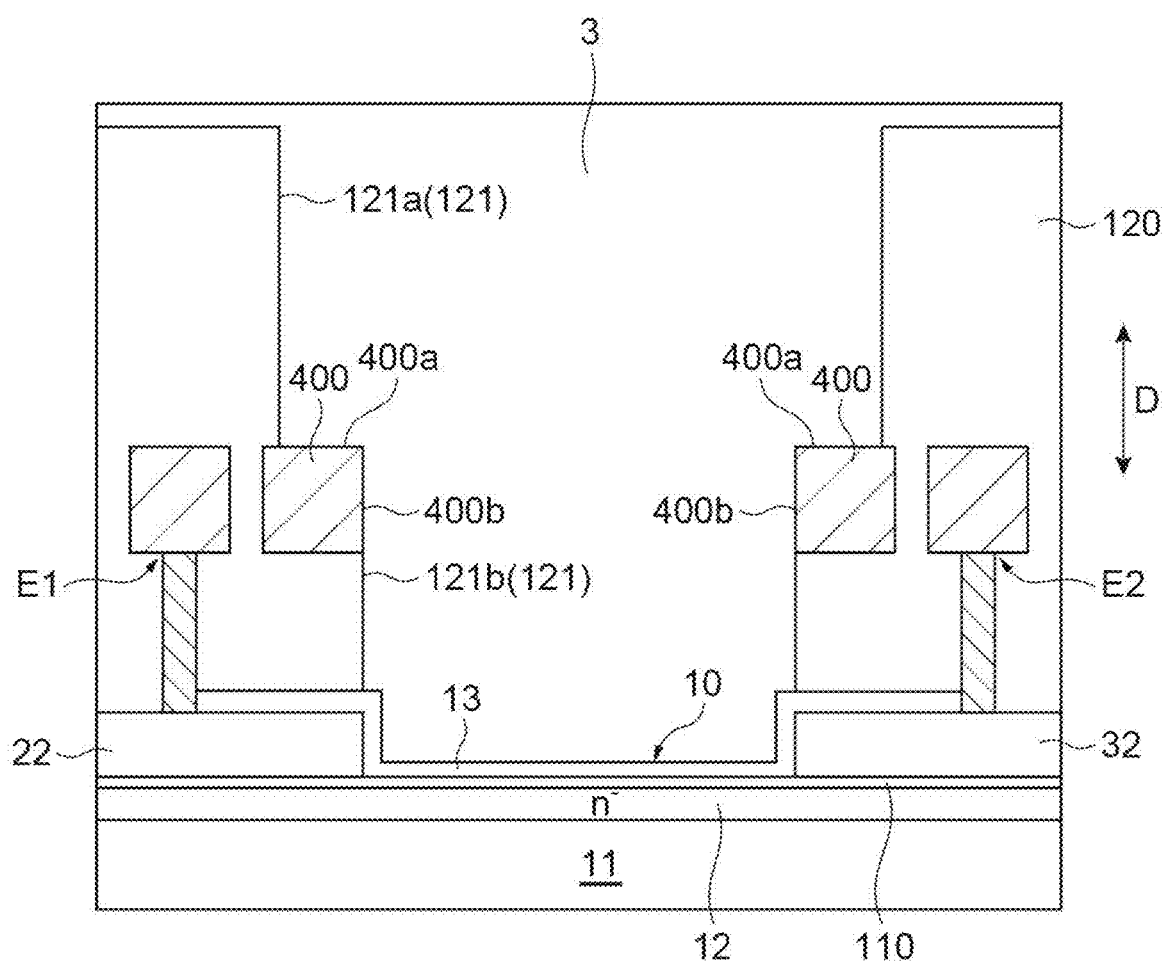
FIG. 10 is a view schematically showing a cross-sectional configuration of a main part of the detection unit including a third modification example of the reference electrode.

FIG. 10 is a view schematically showing a cross-sectional configuration of a main part (a peripheral portion of the sensing section 10) of a detection unit 5 including the reference electrode 400. As shown in FIG. 10, the passivation layer 120 has an opening 121 formed to include the sensing section 10 when viewed in the thickness direction D. The sensitive film 13 is in contact with the substance adsorption film 3 that has entered the opening 121 through the opening 121. The opening 121 includes a first opening portion 121a and a second opening portion 121b. The first opening portion 121a extends from the upper surface of the passivation layer 120 to an upper surface 400a of the reference electrode 400. The second opening portion 121b communicates with the first opening portion 121a and extends to the upper surface of the sensitive film 13 (the surface opposite to the semiconductor substrate 100).

The reference electrode 400 includes a portion inside the opening 121 and in contact with the substance adsorption film 3. In the present embodiment, a part of the upper surface 400a and an inner side surface 400b of the reference electrode 400 are exposed inside the opening 121 and are in contact with the substance adsorption film 3. A part of the upper surface 400a of the reference electrode 400 constitutes a part of a bottom surface of the first opening portion 121a. The inner side surface 400b of the reference electrode 400 constitutes a part of an inner surface of the second opening portion 121b.

As an example, the reference electrode 400 is provided on the same layer (for example, the first wiring layer described above) as metal wiring E1 for applying a voltage to the ICG electrode 22 and metal wiring E2 for applying a voltage to the TG electrode 32. In this way, by providing the reference electrode 400 on the same layer as the metal wirings E1 and E2, it is possible to utilize a layer above the first wiring layer (for example, in the above-described embodiment, the second wiring layer in which the reference electrode 4 is arranged) as a layer for arranging metal wiring for applying a voltage to the RD portion 41, the RG electrode 42, or the like. Accordingly, a degree of freedom in designing the metal wiring can be improved. Further, it is possible to form the metal wiring with higher positional accuracy in a case in which the metal wiring is arranged in the first wiring layer close to the main surface of the semiconductor substrate 100 than in a case in which the metal wiring is arranged in the second wiring layer far from the main surface of the semiconductor substrate 100. Therefore, by arranging the reference electrode 400 on the first wiring layer, it is possible to improve the positional accuracy of the reference electrode 400. Further, by bringing the plurality of surfaces (the upper surface 400a and the inner side surface 400b) of the reference electrode 400 into contact with the substance adsorption film 3, it is possible to more reliably bring the substance adsorption film 3 and the reference electrode 400 into contact with each other.

Next, an example of a method for manufacturing the smell sensor including the reference electrode 400 will be described. First, the ion sensor 2 in which the sensing section 10 provided with the sensitive film 13 is formed on the semiconductor substrate 100 is prepared. Subsequently, the reference electrode 400 is disposed on the semiconductor substrate 100 (the ion sensor 2) to be separated from the sensitive film 13 at the outer edge portion of the sensing section 10 viewed in the thickness direction D. Subsequently, the passivation layer 120 which covers the semiconductor substrate 100 (the ion sensor 2) and the reference electrode 400 is formed. Note that the passivation layer 120 may be formed stepwise by being divided a plurality of times. For example, after a first passivation layer that covers the semiconductor substrate 100 and the sensitive film 13 is formed, the reference electrode 400 may be arranged on the first passivation layer, and then a second passivation layer that covers the reference electrode 400 may be formed, to form the passivation layer 120. In this way, the passivation layer 120 is formed on the ion sensor 2 to cover the reference electrode 4.

Subsequently, by etching the passivation layer 120, the opening 121 for exposing at least a part of the sensitive film 13 (in the present embodiment, a part of the upper surface of the sensitive film 13) and at least a part of the reference electrode 400 (in the present embodiment, a part of the upper surface 400a and the inner side surface 400b) to the outside is formed.

Subsequently, the substance adsorption film 3 is formed from the reference electrode 400 to the sensitive film 13 at least inside the second opening portion 121b. In the present embodiment, as shown in FIG. 10, the substance adsorption film 3 is provided to cover the passivation layer 120 and is in contact with the sensitive film 13 and the reference electrode 400 in the opening 121. That is, the reference electrode 400 (a part of the upper surface 400a and the inner side surface 400b) and the sensitive film 13 provided in the sensing section 10 are connected to each other by a part of the substance adsorption film 3 that has entered the opening 121. That is, the substance adsorption film 3 is at least connected to a portion from the reference electrode 400 to the sensitive film 13 provided in the sensing section 10. Thus, in the above manufacturing method, the substance adsorption film 3 is provided to cover the sensitive film 13 and the reference electrode 400 after the reference electrode 400 is disposed. As described above, the smell sensor including the plurality of detection units 5 having the structure shown in FIG. 10 (that is, the structure in which the reference electrode 400 is embedded inside the substance adsorption film 3) can be obtained. Further, in this case, by disposing the reference electrode 400 at the outer edge portion of the sensing section 10 viewed in the thickness direction D, and thus by forming the common opening 121 in the reference electrode 400 and the sensitive film 13, it is possible to realize a configuration in which the reference voltage Vref can be applied to the substance adsorption film 3 disposed on the sensitive film 13.

According to the reference electrode 400 of the third modification example described above, the reference voltage Vref can be appropriately applied to the substance adsorption film 3 inside the opening 121 provided on the sensing section 10. For example, in a case in which the reference electrode and the substance adsorption film 3 are connected to each other through an opening different from the opening 121 (an opening such as the above-described opening 120b), a peak portion (a portion from the reference electrode toward the upper surface of the passivation layer 120 through the above-described different opening) and a valley portion (a portion from the upper surface of the passivation layer 120 toward the sensitive film 13 through the opening 121) are included in a path from the reference electrode to the sensitive film 13 via the substance adsorption film 3. As a result, there is a high possibility that the substance adsorption film 3 will be broken. On the other hand, according to the reference electrode 400, the substance adsorption film 3 and the reference electrode 400 can be connected to each other in the opening 121. That is, the above-described peak portion and valley portion and the like are not included in the path from the reference electrode 400 to the sensitive film 13 via the substance adsorption film 3. Accordingly, it is possible to prevent the substance adsorption film 3 from being broken as described above.

Second Embodiment

Figure 11:
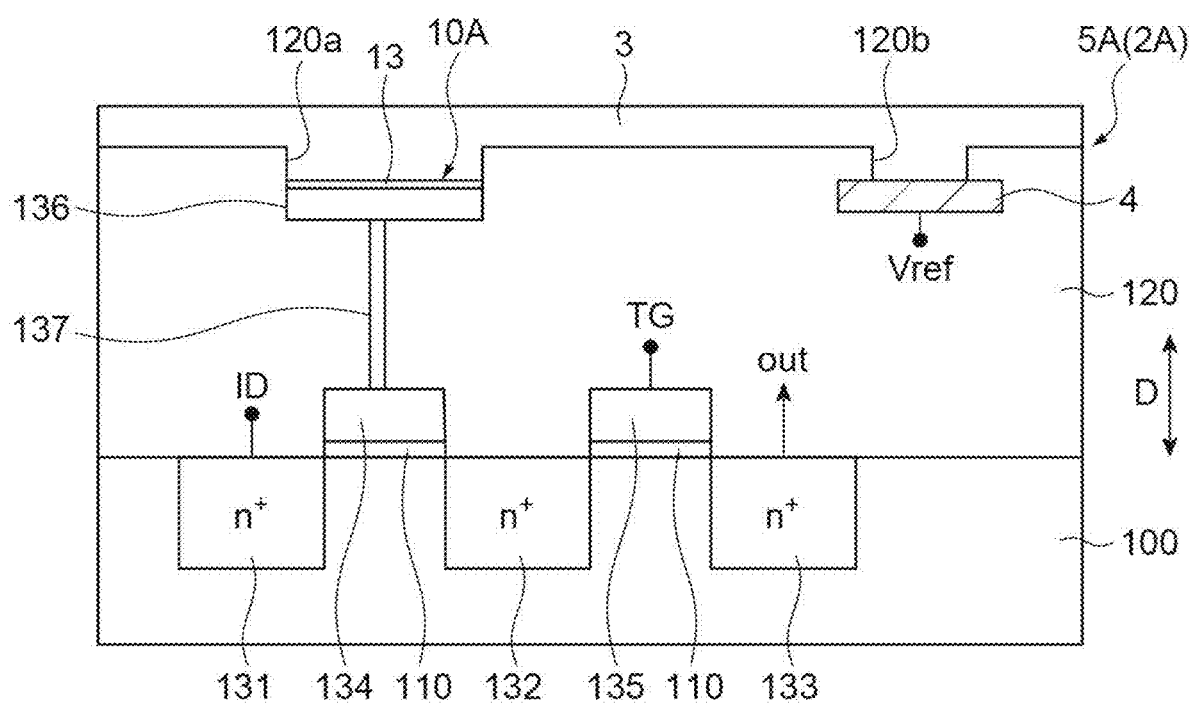
FIG. 11 is a view schematically showing a cross-sectional configuration of a detection unit of a smell sensor according to a second embodiment.

FIG. 11 is a view schematically showing a cross-sectional configuration of a detection unit 5A of a smell sensor according to a second embodiment. The smell sensor of the second embodiment is different from the smell sensor 1 of the first embodiment in that a so-called ISFET type ion sensor 2A is provided instead of the ion sensor 2 which is a so-called charge transfer type CMOS image sensor. Other configurations are the same as those of the smell sensor 1. The ion sensor 2A is different from the ion sensor 2 in that the ion sensor 2A includes a detection unit 5A that employs an ISFET type measurement method as a unit detection element, instead of the detection unit 5 that employs a charge transfer type measurement method as a unit detection element.

In the detection unit 5A, first conductive type (here, n type) of three $n^+$ type regions 131 to 133 are formed on one main surface side of the semiconductor substrate 100. Further, two gate electrodes 134 and 135 are formed on the main surface of the semiconductor substrate 100 with an insulating protective film 110 interposed therebetween. The gate electrode 134 is located between the $n^+$ type region 131 and the $n^+$ type region 132. The $n^+$ type region 131, the $n^+$ type region 132, and the gate electrode 134 constitute a MOS transistor. An ID signal (a voltage) is applied to the $n^+$ type region 131 from a control unit (not shown). The gate electrode 135 is located between the $n^+$ type region 132 and the $n^+$ type region 133. A TG signal (a voltage) is applied to the gate electrode 135 from a control unit (not shown). The $n^+$ type region 133 is electrically connected to a measurement circuit (not shown). A conductive member 136 on which the sensitive film 13 is placed is electrically connected to the gate electrode 134 via a conductive connecting member 137. A portion where the sensitive film 13 is provided on the conductive member 136 functions as a sensing section 10A. The sensing section 10A is a region where the sensitive film 13 is exposed to the outside (that is, to the substance adsorption film 3) through the opening 120*a* of the passivation layer 120 which will be described later. The conductive member 136 has, for example, a rectangular shape having substantially the same size as the sensitive film 13 when viewed in the thickness direction D. The sensitive film 13 is formed on an upper surface of the conductive member 136.

Similar to the detection unit 5 of the first embodiment, the insulating passivation layer 120 is formed on the main surface of the semiconductor substrate 100 to cover members provided on the main surface of the semiconductor substrate 100 as described above. Further, the substance adsorption film 3 is provided to cover the passivation layer 120. The passivation layer 120 has the opening 120*a* for exposing the upper surface of the sensitive film 13 to the outside. The sensitive film 13 is in contact with the substance adsorption film 3 through the opening 120*a*. Further, the reference electrode 4 is disposed not to overlap the sensitive film 13 and the gate electrode 135 when viewed in the thickness direction D of the semiconductor substrate 100. Further, the structure shown in FIG. 11 is commonly applied to each detection unit 5A, and thus the distances (the positional relationship) between the sensitive film 13 of each sensing section 10A and the reference electrode 4 viewed in the thickness direction D are substantially the same. The reference electrode 4 is in contact with the substance adsorption film 3 through the opening 120*b* provided in the passivation layer 120. Note that in the example of FIG. 11, the upper surface of the sensitive film 13 and the upper surface of the reference electrode 4 are located at positions recessed toward the semiconductor substrate 100 side with respect to the upper surface of the passivation layer 120, but the sensitive film 13 or the reference electrode 4 may be provided so that the upper surface of the sensitive film 13 or the reference electrode 4 is continuous (flatly connected) with a portion of the passivation layer 120 at which the openings 120*a* and 120*b* are not formed.

Next, the operation principle of the detection unit 5A will be described. First, the outline of the operation principle will be described. When the smell substance is adsorbed on the substance adsorption film 3, the characteristic change of the substance adsorption film 3 occurs, and the membrane potential of the sensitive film 13 changes accordingly. As a result, the potential of the gate electrode 134 electrically connected to the sensitive film 13 changes. The smell detected in the substance adsorption film 3 (that is, the smell substance adsorbed on the substance adsorption film 3) is measured as a change in current or voltage of a signal (an out signal) according to such a potential change of the gate electrode 134. Then, for example, it is possible to specify the detected smell substance by collating such a measurement result with the smell database as described above. Hereinafter, first to third examples of an operation (a driving method) of the detection unit 5A will be described. Here, a method other than these examples may be used as the driving method of the detection unit 5A.

First Example

A first example is a driving method generally employed in ISFETs. The first example is a driving method based on a phenomenon that the magnitude of the current flowing between the $n^+$ type region 131 and the $n^+$ type region 132 changes according to the change in the potential of the gate electrode 134 described above. That is, when the potential of the gate electrode 134 changes according to the character-istic change of the substance adsorption film 3, the magnitude of the current flowing between the $n^+$ type region 131 and the $n^+$ type region 132 changes. Here, the gate electrode 135 is used as a switch, and the TG signal which is applied to the gate electrode 135 is changed, and thus the switch is turned on. That is, the charges of the $n^+$ type region 132 is switched to a state of flowing to the $n^+$ type region 133 via a region (hereinafter referred to as a "TG region") facing the gate electrode 135. Accordingly, the current flowing between the $n^+$ type region 131 and the $n^+$ type region 132 is output as an out signal via the TG region and the $n^+$ type region 133. After that, for example, the out signal is converted into a voltage in a measuring unit (not shown). As a result, the characteristic change of the substance adsorption film 3 is measured as the voltage change of the out signal.

Second Example

In a second example, in a state in which the switch of the gate electrode 135 is turned on, the ID signal which is supplied to the $n^+$ type region 131 is changed, and thus the charges are injected into the $n^+$ type region 131. After that, the injection of the charges into the $n^+$ type region 131 is stopped, and the voltage of the out signal when the injection of the charges is stopped is measured by the measuring unit. As a result, in the measuring unit, the characteristic change of the substance adsorption film 3 is measured as the voltage change of the out signal.

Third Example

Schematically, the third example is a method in which a region of the semiconductor substrate 100 which faces the gate electrode 134 (hereinafter referred to as a "gate region") is caused to function as the ICG region in the charge transfer type detection unit 5 described above, and the $n^+$ type region 132 is caused to function as the FD portion 31 in the detection unit 5. The third example will be described in detail with reference to FIG. 12. As shown in (A) of FIG. 12, the depth of the potential well in the gate region changes according to the potential change of the sensitive film 13. As shown in (B) of FIG. 12, the potential of the $n^+$ type region 131 ("ID" in FIG. 12) is lowered by controlling the ID signal. Accordingly, the $n^+$ type region 131 is charged with the charges. The charges charged in the $n^+$ type region 131 are injected into the $n^+$ type region 132 beyond the gate region. At this time, a potential of the TG region is controlled to be lower than the potential of the $n^+$ type region 131. Therefore, the charges injected into the $n^+$ type region 132 do not reach the $n^+$ type region 133 ("out" in FIG. 12) beyond the TG region.

Figure 12:
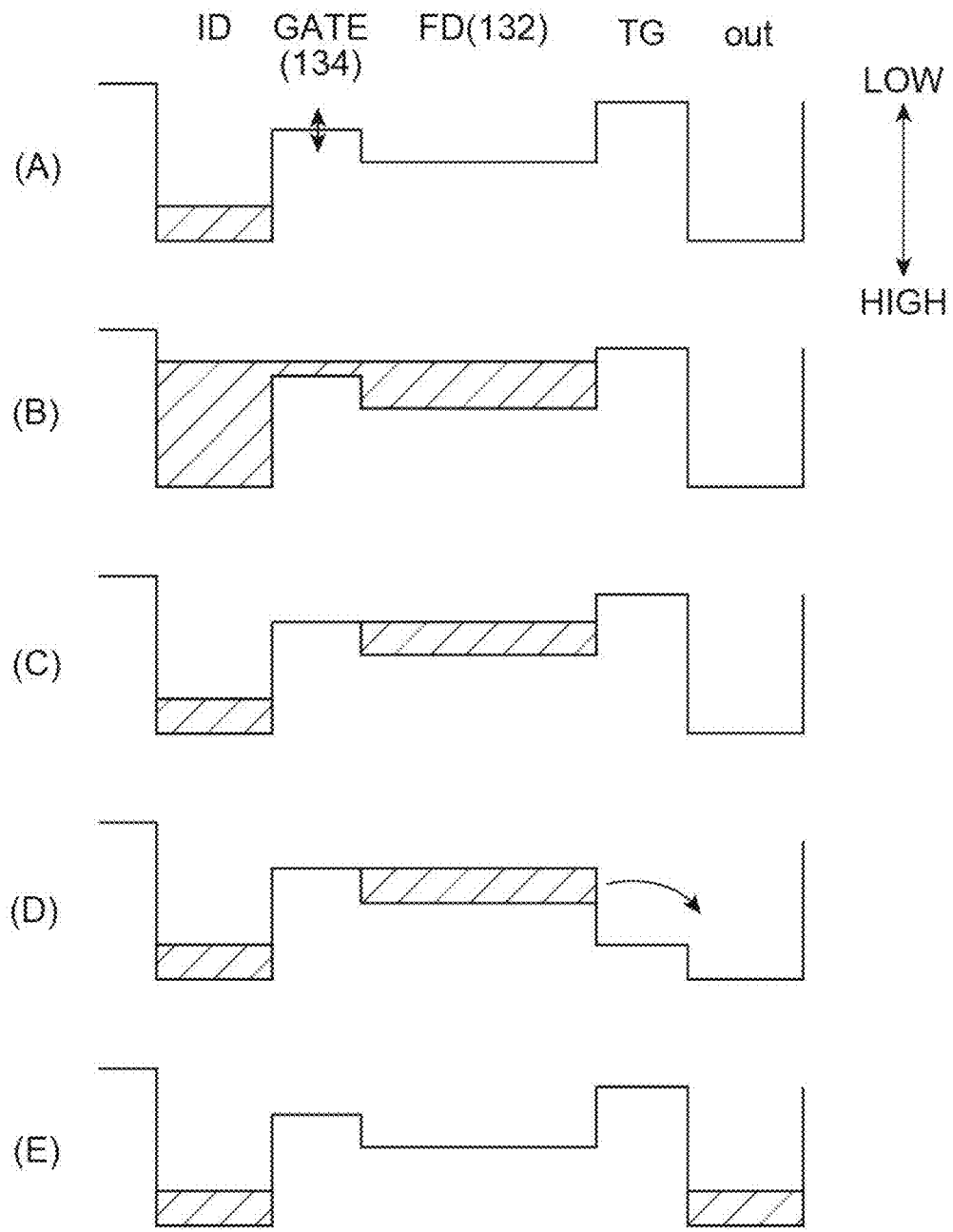
FIG. 12 is a diagram showing a third example of an operation of a detection unit 5A shown in FIG. 11.

Subsequently, as shown in (C) of FIG. 12, the potential of the $n^+$ type region 131 is restored (raised), and thus the charges are extracted from the $n^+$ type region 131. As a result, the charges scooped by the gate region remain in the $n^+$ type region 132. The amount of charges left in the $n^+$ type region 132 corresponds to the depth of the potential well of the gate region (that is, the impedance change of the substance adsorption film 3).

Subsequently, as shown in (D) of FIG. 12, the voltage of the gate electrode 135 is raised, and thus the charges left in the $n^+$ type region 132 are transferred to the $n^+$ type region 133. After that, the voltage of the gate electrode 135 is restored, and thus a state shown in (E) of FIG. 12 is realized. In such a state, a signal according to the amount of charges accumulated in the $n^+$ type region 133 (that is, a signal according to the characteristic change of the substance adsorption film 3) is output as an out signal to the measuring unit.

Even in a case in which the smell sensor of the second embodiment is configured based on the ion sensor 2A including the detection unit 5A as a unit detection element as described above, the same effect as that of the smell sensor 1 described above can be exhibited. Further, the smell sensor of the second embodiment is obtained by the same manufacturing method as the above-described manufacturing method of the smell sensor 1. Note that the conductive member 136 and the connecting member 137 may be omitted. In that case, the sensitive film 13 constituting the sensing section 10A may be directly formed on the gate electrode 134. However, by providing the conductive member 136 and the connecting member 137, it is possible to cause the upper surface of the sensitive film 13 to be close to the surface of the passivation layer 120, and thus an effect that the depth of the opening 120a can be reduced is exhibited.

Although the preferred embodiments of the present disclosure have been described above in detail, the present disclosure is not limited to the above embodiments. For example, in the ion sensor, the plurality of sensing sections (detection units) may be arranged two-dimensionally or may be arranged one-dimensionally. Further, the ion sensor may have only one sensing section (detection unit).

Further, in the above-described embodiment, the semiconductor substrate 100 is used as the substrate on which the sensing section 10 is formed, but the substrate on which the sensing section 10 is formed does not necessarily have to be a semiconductor substrate. For example, the substrate may be a substrate other than a semiconductor, which has a semiconductor region (for example, a semiconductor film or the like) on the surface.

REFERENCE SIGNS LIST

1 Smell sensor
2, 2A Ion sensor
3 Substance adsorption film
4, 200, 300, 400 Reference electrode
5, 5A Detection unit
10, 10A Sensing section
13 Sensitive film
100 Semiconductor substrate
120 Passivation layer
120a Opening (first opening)
120b Opening (second opening)
121 Opening
121a First opening portion
121b Second opening portion

The invention claimed is:

1. A smell sensor comprising:
an ion sensor in which at least one sensing section provided with a sensitive film configured to change a potential in accordance with a state of a measurement target is formed on a substrate;
a substance adsorption film as the measurement target, disposed on the sensitive film and configured to change the state with adsorption of a smell substance; and
a reference electrode configured to apply a reference voltage to the substance adsorption film,
wherein the reference electrode is disposed to be separated from the sensitive film and not to overlap the sensing section when viewed in a thickness direction of the substrate, and
wherein the reference electrode is provided on at least a surface of the substance adsorption film opposite to the substrate.

2. The smell sensor according to claim 1, further comprising:
a passivation layer provided to cover the ion sensor,
wherein the substance adsorption film is provided to cover the passivation layer,
wherein the sensitive film is in contact with the substance adsorption film through a first opening provided in the passivation layer, and
wherein the reference electrode is provided between the substance adsorption film and the substrate, and is in contact with the substance adsorption film through a second opening provided in the passivation layer.

3. The smell sensor according to claim 1, further comprising:
a passivation layer provided to cover the ion sensor,
wherein the substance adsorption film is provided to cover the passivation layer,
wherein the sensitive film is in contact with the substance adsorption film through an opening provided in the passivation layer, and
wherein the reference electrode is disposed at an outer edge portion of the sensing section when viewed in the thickness direction of the substrate, and includes a portion exposed inside the opening and in contact with the substance adsorption film.

4. The smell sensor according to claim 1,
wherein the ion sensor has a plurality of sensing sections arranged one-dimensionally or two-dimensionally on the substrate, and
wherein one substance adsorption film is disposed on the sensitive films of two or more sensing sections.

5. The smell sensor according to claim 1,
wherein the ion sensor has a plurality of sensing sections arranged one-dimensionally or two-dimensionally on the substrate, and
wherein a plurality of substance adsorption films are disposed on the sensitive films of different sensing sections.

6. The smell sensor according to claim 1,
wherein the ion sensor has a plurality of sensing sections arranged one-dimensionally or two-dimensionally on the substrate, and
wherein the reference electrode is disposed such that distances between the sensitive film of each of the plurality of sensing sections and the reference electrode are substantially the same.

7. A method for manufacturing a smell sensor comprising:
a step of preparing an ion sensor in which a sensing section provided with a sensitive film configured to change a potential in accordance with a state of a measurement target is formed on a substrate;
a step of disposing, on the sensitive film, a substance adsorption film as the measurement target configured to change the state with adsorption of a smell substance; and
a step of disposing a reference electrode configured to apply a reference voltage to the substance adsorption film to be separated from the sensitive film and not to overlap the sensing section when viewed in a thickness direction of the substrate,
wherein the substance adsorption film is provided to cover the sensitive film and the reference electrode after the reference electrode is disposed.

8. The method for manufacturing a smell sensor according to claim 7, further comprising:
   a step of forming a passivation layer on the ion sensor to cover the reference electrode after the reference electrode is disposed; and
   a step of forming, in the passivation layer, a first opening for exposing at least a part of the sensitive film to the outside and a second opening for exposing at least a part of the reference electrode to the outside,
   wherein the substance adsorption film is provided to cover the passivation layer after the first opening and the second opening are formed, is in contact with the sensitive film through the first opening, and is in contact with the reference electrode through the second opening.

9. The method for manufacturing a smell sensor according to claim 7, further comprising:
   a step of forming a passivation layer on the ion sensor to cover the reference electrode after the reference electrode is disposed at an outer edge portion of the sensing section when viewed in the thickness direction of the substrate; and
   a step of forming, in the passivation layer, an opening for exposing at least a part of the sensitive film and at least a part of the reference electrode to the outside,
   wherein the substance adsorption film is provided to cover the passivation layer after the opening is formed, and is in contact with the sensitive film and the reference electrode in the opening.

10. A method for manufacturing a smell sensor comprising:
    a step of preparing an ion sensor in which a sensing section provided with a sensitive film configured to change a potential in accordance with a state of a measurement target is formed on a substrate;
    a step of disposing, on the sensitive film, a substance adsorption film as the measurement target configured to change the state with adsorption of a smell substance; and
    a step of disposing a reference electrode configured to apply a reference voltage to the substance adsorption film to be separated from the sensitive film and not to overlap the sensing section when viewed in a thickness direction of the substrate,
    wherein at least a part of the reference electrode is provided to cover a part of the substance adsorption film after the substance adsorption film is disposed.

11. A smell sensor comprising:
    an ion sensor in which at least one sensing section provided with a sensitive film configured to change a potential in accordance with a state of a measurement target is formed on a substrate;
    a substance adsorption film as the measurement target, disposed on the sensitive film and configured to change the state with adsorption of a smell substance; and
    a reference electrode configured to apply a reference voltage to the substance adsorption film,
    wherein the reference electrode is disposed to be separated from the sensitive film and not to overlap the sensing section when viewed in a thickness direction of the substrate,
    wherein the ion sensor has a plurality of sensing sections arranged one-dimensionally or two-dimensionally on the substrate, and
    wherein one substance adsorption film is disposed on the sensitive films of two or more sensing sections.

12. The smell sensor according to claim 11, further comprising:
    a passivation layer provided to cover the ion sensor,
    wherein the substance adsorption film is provided to cover the passivation layer,
    wherein the sensitive film is in contact with the substance adsorption film through a first opening provided in the passivation layer, and
    wherein the reference electrode is provided between the substance adsorption film and the substrate, and is in contact with the substance adsorption film through a second opening provided in the passivation layer.

13. The smell sensor according to claim 11, further comprising:
    a passivation layer provided to cover the ion sensor,
    wherein the substance adsorption film is provided to cover the passivation layer,
    wherein the sensitive film is in contact with the substance adsorption film through an opening provided in the passivation layer, and
    wherein the reference electrode is disposed at an outer edge portion of the sensing section when viewed in the thickness direction of the substrate, and includes a portion exposed inside the opening and in contact with the substance adsorption film.

14. The smell sensor according to claim 11,
    wherein the ion sensor has a plurality of sensing sections arranged one-dimensionally or two-dimensionally on the substrate, and
    wherein a plurality of substance adsorption films are disposed on the sensitive films of different sensing sections.

15. The smell sensor according to claim 11,
    wherein the ion sensor has a plurality of sensing sections arranged one-dimensionally or two-dimensionally on the substrate, and
    wherein the reference electrode is disposed such that distances between the sensitive film of each of the plurality of sensing sections and the reference electrode are substantially the same.

16. A smell sensor comprising:
    an ion sensor in which at least one sensing section provided with a sensitive film configured to change a potential in accordance with a state of a measurement target is formed on a substrate;
    a substance adsorption film as the measurement target, disposed on the sensitive film and configured to change the state with adsorption of a smell substance; and
    a reference electrode configured to apply a reference voltage to the substance adsorption film,
    wherein the reference electrode is disposed to be separated from the sensitive film and not to overlap the sensing section when viewed in a thickness direction of the substrate,
    wherein the ion sensor has a plurality of sensing sections arranged one-dimensionally or two-dimensionally on the substrate, and
    wherein a plurality of substance adsorption films are disposed on the sensitive films of different sensing sections.

17. The smell sensor according to claim 16, further comprising:
    a passivation layer provided to cover the ion sensor,
    wherein the substance adsorption film is provided to cover the passivation layer, wherein the sensitive film is in contact with the substance adsorption film through a first opening provided in the passivation layer, and wherein the reference electrode is provided between the substance adsorption film and the substrate, and is in contact with the substance adsorption film through a second opening provided in the passivation layer.

18. The smell sensor according to claim 16, further comprising:

a passivation layer provided to cover the ion sensor, wherein the substance adsorption film is provided to cover the passivation layer, wherein the sensitive film is in contact with the substance adsorption film through an opening provided in the passivation layer, and wherein the reference electrode is disposed at an outer edge portion of the sensing section when viewed in the thickness direction of the substrate, and includes a portion exposed inside the opening and in contact with the substance adsorption film.

19. The smell sensor according to claim 16, wherein the ion sensor has a plurality of sensing sections arranged one-dimensionally or two-dimensionally on the substrate, and wherein the reference electrode is disposed such that distances between the sensitive film of each of the plurality of sensing sections and the reference electrode are substantially the same.

20. A smell sensor comprising:

an ion sensor in which at least one sensing section provided with a sensitive film configured to change a potential in accordance with a state of a measurement target is formed on a substrate;

a substance adsorption film as the measurement target, disposed on the sensitive film and configured to change the state with adsorption of a smell substance; and a reference electrode configured to apply a reference voltage to the substance adsorption film, wherein the reference electrode is disposed to be separated from the sensitive film and not to overlap the sensing section when viewed in a thickness direction of the substrate, wherein the ion sensor has a plurality of sensing sections arranged one-dimensionally or two-dimensionally on the substrate, and wherein the reference electrode is disposed such that distances between the sensitive film of each of the plurality of sensing sections and the reference electrode are substantially the same.

* * * * *